(12) United States Patent
John

(10) Patent No.: US 6,211,430 B1
(45) Date of Patent: Apr. 3, 2001

(54) FBLATE PROMOTER

(75) Inventor: Maliyakal E. John, Middleton, WI (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 08/467,504

(22) Filed: Jun. 6, 1995

(51) Int. Cl.[7] ............................... A01H 5/00; A01H 5/10; C12N 15/82

(52) U.S. Cl. ................... 800/205; 800/250; 800/255; 800/DIG. 27; 800/DIG. 63; 435/69.1; 435/70.1; 435/172.3; 435/419; 536/24.1

(58) Field of Search .................... 536/23.1, 24.1; 435/69.1, 70.1, 172.3, 240.4, 320.1, 419; 800/205, 250, 255, DIG. 27, DIG. 63

(56) References Cited

U.S. PATENT DOCUMENTS

| | | | |
|---|---|---|---|
| 5,474,925 | * 12/1995 | John et al. | 435/172.3 |
| 5,495,070 | 2/1996 | John | 800/205 |
| 5,521,078 | 5/1996 | John | 435/172.3 |

OTHER PUBLICATIONS

M. E. John, "An efficient method for isolation of RNA and DNA from plants containing polyphenolics," *Nucl. Acids Res.* 20(9):2381, 1992.

M. E. John and J. McD. Stewart, "Genes for jeans: biotechnological advances in cotton," *TIBTECH* 10(5):165–170, 1992.

M. E. John and L. J. Crow, "Gene expression in cotton (*Gossypium hirsutum* L. ) fiber: Cloning of the mRNAs," *Proc. Natl. Acad. Sci. USA* 89:5769–5773, 1992.

A. Klausner, "Researchers Cotton to New Fiber Findings," *Bio/Technology* 3:104–105, 1985.

L. McHenry and P. J. Fritz, "Comparison of the structure and nucleotide sequences of vicilin genes of cocoa and cotton raise questions about vicilin evolution," *Plant Mole. Biol.* 18:1173–1176, 1992.

F. Sagliocco, et al., "Sequence of an *rbcS* gene from cotton, "*Plant Mol. Biol.* 17:1275–1276, 1991.

R. B. Turley, et al., "Characterization of a cDNA clone encoding the complete amino acid sequence of cotton isocitrate lyase," *Biochimica et Biophysica Acta* 1049:223–226, 1990.

Lewin (1987) Science 237: 1570.*

Kim et al. (1994) Plant Mol. Biol. 24: 105–117.*

* cited by examiner

*Primary Examiner*—Elizabeth F. McElwain

(57) ABSTRACT

A gene construct comprising an FbLate promoter is disclosed. A method of obtaining an FbLate promoter and a plant, cell and seed comprising an FbLate promoter are also disclosed.

5 Claims, 8 Drawing Sheets

BS = pBLUESCRIPT SK+ PHAGEMID
FBL2 ORF = FBLATE 2 OPEN READING FRAME
FBL2p 2.3 = 2.3Kb FBLATE 2 PROMOTER REGION

I: THE 12.7 kb INSERT OF pSKSIFbLate2-82A PLASMID

◺ = WEAK HYBRIDIZATION TO FbLATE-2 cDNA

▨ = STRONG HYBRIDIZATION TO FbLate-2 cDNA

II: Nco PROMOTER FRAGMENT (4.0 kb)

▨ = SEQUENCED REGION

III: Nco-Pst PROMOTER FRAGMENT (2.3 kb)

IV: 1.3 kb PROMOTER REGION

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 974 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
CCAAAACATG AGAAGCCTGA AATGTACAAG GAGGAAAAAC AAAAACCCTG CAAACATCAT      60

GAAGAGTACC ACGAGTCACG CGAATCGAAG GAGCACGAAG AGTACGATAA AGAAAAACCC     120

GATTTCCCCA AATGGGAAAA GCCTAAAGAG CACGAGAAAC ACGAAGTCGA ATATCCGAAA     180

ATACCCGAGT ACAAGGACAA ACAAGATGAG GATAAGGAAC ATAAAAATGA AGAGTACCAC     240

GAATCACGTG AATCGAAGGA GCACGAAGAA TACGAGAAAG AAAAACCCGA GTTCCCCAAA     300

CGGGAAAAGC CTAAAGAGCA CGAGAAACAC GAAGTCGAAT ATTCGGAAAT ACCCGAGTAC     360

AAGGAAAAGG AAGATAAGAG TAAGAAACAT AAAGATGAAG AGTGCCAGGA GTCACACGAA     420

TCGAAAGAGC ACGAAGAGTA CGAGAAAGAA AAACCCGATT TCCCCAAATG GAAAAGCCT     480

AAAGGGCACG AGAAACATAA AGCCGAATAT CCGAAAATAC CTGAGTGCAA GGAAAAACTA     540

GATGAGGATA AGGAACATAA ACATGAGTTC CCAAAGCATG AAAAAGAAGA GGAGAAGAAA     600

CCTGAGAAAG GCATAGTACC CTGAGTGGGT TAAAATGCCT GAATGGCCGA AGTCCATGTT     660

TACTCAGTCT GGCTCGAGCA CTAAGCCTTA AGCCATATGA CACTGGTGCA TGTGCCATCA     720

TCATGCAGTA ATTTCATGGG ATATTGTAAT TATATTGTTA ATAAAAAAGA TGGTGAGTGG     780

GAAATGTGTG TGTGCATTCA TCCATGTAGC AATGCTGAAT CTCTTTGCAT GCATAGAGAT     840

TCTGAATGGT TATAGTTTAT GTTATATCGT TTGTTCTAGT GAAATTAATT TTGAATGTTG     900

TATGTAATGT TAACATCACT TGGCTTGATT TATGTTTTAA TGAAGTTTAT GTTGTGTATT     960

TTACTTTAAA AAAA                                                      974
```

(2) INFORMATION FOR SEQ ID NO:2:

(i) SEQUENCE CHARACTERISTICS:
      (A) LENGTH: 645 base pairs (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

| | | | | | | |
|---|---|---|---|---|---|---|
| AATCTAAAGA | GCACGAAGAG | TACGAGAAAG | AAAAACCCAA | TTTCCCCAAA | GGGGAAAAGC | 60 |
| CCAAAGAGCA | CGAGAAACAT | GAAGTCGAAT | ATCCGAAAAT | ACCCGGGTAC | AAGGAAAAAC | 120 |
| AAGATGAGGG | CAAGGAACAT | AAACATGATG | AGTGCCACGA | GTCACACGAA | TCGAAGGAGC | 180 |
| ACGAAGAGTA | CGAGAAAGAA | AAACCCAATT | TCCCCAAAGG | GGAAAAGCCT | AAAGAGCATG | 240 |
| AGAAACACGA | AGTCGAATAT | CCGAAAATAC | CGAATACAA | GGAAAAACAA | GATGAGGGTA | 300 |
| AGGAACATAA | ACATGAGTTC | CAAAAGCATG | AAAAAGAAGA | GGAGAAAAAA | CCTGAGAAAA | 360 |
| AGGCAGAGTA | CTCTGAGTGG | CCAAAGTACA | TGTTTACTCA | ATCTGGCTCG | GGCACTAAGC | 420 |
| CTTGAACCAT | ATGACACTGG | TGCATGTGCC | ATCATCATGC | AGTAATTTCA | TGGTATATCT | 480 |
| TAATTATATG | GTTAATAAAA | AAAAGATGGT | GAGTGAATAA | TGTGCGTGCA | TTCCTCCATG | 540 |
| CACCAATGGT | GAATCTCTTT | GCATACATAG | AGATTCTGAA | TGATTATAGT | TTATGTTATA | 600 |
| TTTTATGTTG | TAGTGAAATT | AATTTTGAAT | GTTGTTTTTA | AAAAA | | 645 |

(2) INFORMATION FOR SEQ ID NO:3:

(i) SEQUENCE CHARACTERISTICS:
        (A) LENGTH: 3974 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
| CTGCAGACTT | AGGATTGGAT | GGCGTTCAGG | AGCTTGGATT | GGTTTTCTCA | CATCATATTT | 60 |
| TATTAAATAA | TTATTAATTA | AAATTTATGG | ACTTTTGGAC | TGTCTGACTA | ATTTTCAGAA | 120 |
| TTTTATTTTG | GTTTTGGGTT | TTGTTGAGTT | TTTTAGATAA | TTATTTTAAA | TATTCTGCAT | 180 |
| AATTTTTCTG | TTATTTGAAA | AGGATGTTCG | AATTTTTTTT | CAAAATTGAA | ACGTTTAAGA | 240 |
| ATTTTTACTA | CTGCAAATTC | AGAATAAGTG | AATTTGTTTT | TTAGAAAGAT | TAAATAAGTT | 300 |
| AGTATTACGA | TTTTTAGTTT | GATTTGGTGG | AAAGTAATGT | ATGTTTTTGA | ACATAATTAT | 360 |
| TTGACAATAA | TTAAGTTTTC | TAGGAAATAA | ACGGAAATAT | CTTCTTTTTT | TTTTGTAAAA | 420 |
| TTACTAATGC | AAGAACAAAC | AACGTTTTGG | GAAGCAAATA | ATCTAGCTTT | AAGTAGTCAG | 480 |
| TGTAACTCTC | AAAATCTGGT | CATAACTTCT | AGGCTGAGTT | TGCTGTGCTA | CAGTAGTAAG | 540 |
| TCTATAGAAA | CTTACCTGAC | AAAACGACAT | GACGTCAGGG | TCGAATCTAC | AACTTTTCCT | 600 |
| TTTTCTTCAA | TTAACATATG | GTTGATTCAA | GTTCCGATCT | ATAATAATTT | ATTACGATTT | 660 |
| ATCAATTTCA | ATTACCTTAT | ATCATCCTAT | TATAAATATA | AGTCAGTTCA | ATTCAGTTTT | 720 |
| CGAAAGTTCC | CTAAAATTTT | GAATTTTATT | AAATTTATTC | CCTAAAACCG | AAATAGTGAT | 780 |
| ATCTTTCAAA | TTTAAGTTTC | ATTTTTCAAT | CCGATTTCAA | TTTCATCCTT | TTATAACTCT | 840 |
| CTATGATCTA | TAATTACATA | AATTTCAAAC | TAATTTTGAA | ATATATACAC | TTTAGTCCCT | 900 |
| AAGTTCAAAA | CTATAAATTT | TCACTTTAGA | AATTAATCAT | TTTTCACATC | TAAGCATCAA | 960 |
| ATTTAACCAA | ATGACACAAA | TTTCATGATT | AGTTAGATCA | AGCTTTTGAG | TCTTCAAAAA | 1020 |
| CATAAAAATT | ACAAAAAAAA | AAAAACAAAC | TTAAAATCAT | TTATCAATTT | GAACAACAAA | 1080 |

```
GCTTGGCCGA ATGCTAAGAG CTTAAAAATG GCTTCTTTTG TTTCTTTTTG TTGCAAACGG    1140

TGGAGAGAAG AGGGAAATGA AGATTGACCA TATTTTTTTA TTATGTTTTA ACATATAATA    1200

TTAATAATTT AATCATAATT ATACTTTGGT GAATGTGACA GTGGGGAGAT ACGTAAAGTA    1260

TATAACATTA TACTTTTTGC AAGCAGTTGG CTGGTCTATC CAAGAGTGAT CAAAGTTTGA    1320

GCTGCCTTCA ATGAGCCAAT TTTTGCCCAT AATGGATAAA GGCAATTTGT TTAGTTCAAC    1380

TGCTCACAGA ATAATGTTAA ATGAAATTA AAATAAGGTG GCCTGGTCAC ACACACACAA     1440

AAAAAAAACT AATGTTGGTT GGTTGAATTT TATATTACGG AATGTAATGT TATATTTTAA    1500

AATAAAATTA TGTTATTTAG ATTCTTAATA TTTTGAGCAT TCCATACTAT AATCTCGTAT    1560

ACATAATATT AAAATATAGT AATATAAAGT GTAATTAACT TTAAATTACA AGCATAATAT    1620

TAAATTTTGA ATCAATTAAT TTTTATTTCT ATTATTTTAA TTAATTTAGT CTATTTTTTC    1680

AAAATAAAAT TTAAATCTAA ATAAAAATAA TTTTTCCTTA ATATTATTAA TAAATTTATT    1740

TCAACATCAT ATATTTACTT ATTAATACAT AAATTATAAT AATTTATCAT AATTTTATGG    1800

AAAATTGAGAC CAAGAAACAT TAAGAGAACA AATTCTATAA CAAAGACAAT TTAGTAAAAA   1860

TGTACTTTTA GGTAATTTTA AGTACTCTTA ACCAAACACA AAAATTCAAA TCAAATGAAC    1920

CAAATAAGAT AATATAACAT ACAGAATATC CTACTTGTAT TCTTACATTC CCGTAATCAT    1980

ATTATGAAAA GTAATATTAT ATTACCTGAG CCAAATGCTC TCACAAACTA TTATCCAAAA    2040

AAAAAATGTT GAATATAATT TTTATAACAT TTTTTCATAT ATTTGCAAGA TTATATTTTG    2100

TATATTTACG TAAAAATATT TGACATAGAT TGAACACCTT CTTAACATAA TCCCACCATA    2160

AGTCAAGTAT GTAGATGAGA AATTGGTACA AACAACGTGG GGCCAAATCC CACCAAACCA    2220

TCTCTCATCC TCTCCTATAA AAGGCTAGTT ACACATACAC AACAATCCAC ACACAAATAC    2280

ACTCAAAATT CTTTGCTTTG TATTTCGGTT AACCATGGCT CATAACACTC GTCACCCTTT    2340

CTTCCTTTTC CAACTTTTAC TCATTAGTGT CTCACTAATG ATCGGTAGCC ACACCGTCTC    2400

GACAGCGGCT CGACGTTTAT TCGAGACACA AACAACCTCA TCGGAGTTGC CACAATTAGC    2460

TTCAAAATAC GAAAAGCAGG AAGAGTCTGA ATATGAAAAG CCGGAATACA AACAGCCAAA    2520

GTATGACGAA GAGTACCCAA ACATGAGAA GCCTGAAATT CACAAGGAGG AAAAACAAAA    2580

ACCGTGCAAG CAACATGAAG AGTACCACGA GTCACACAAA TCGAAGGAGC ACGAAGAGTA    2640

CCAGAAAGAA AAACCCGAGT TCCCCAAATT GGAAAAGCCT AAAGAGCACG AGAAACACGA    2700

AGTCGAATAT CCGAAAATAC TCGAGTACAA GGAAAACCAA GATGAGGGTA AGGAACATAA    2760

ACATGAAGAG TACCACGAAT CACGTGAATC GAAGGAGCAC GAAGAGTACG AGAAAGAAAA    2820

ACCCGAGTTC CCCAAATTGG AAAAGCCTAA AGAGCACGAG AAACACGAAG TCGAATATCC    2880

GGAAATACCC GAGTACAAGG AAAAGCAAGA TGAGGGTAAG GAACATAAAC ATGAGGAGTG    2940

CCACAAGTCA CACGAATCGA AGGAGCACGA AGAGTACGAG AAAGAAAAAC CAATTTCCC     3000

CAAAGGGGAA AAGCCCAAAG AGCACGAGAA ACATGAAGTC GAATATCCGA AAATACCCGA    3060

GTACAAGGAA AAACAAGATG AGGGCAAGGA ACATAAACAT GATGAGTGCC ACGAGTCACA    3120

CGAATTGAAG GAGCACGAAG AGTACGAGAA AGAAAAACCC AATTTCCCCA AGGGGAAAA     3180

GCCTAAAGAG CACGAGAAAC ACGAAGTCGA ATATCCGAAA ATACCCGAGT ACAAGGAAAA    3240

ACAAGATGAG GGTAAGGAAC ATAAACATGA GTTCCAAAAG CATGAAAAAG AAGAGGAGAA    3300

AAAACCTGAG AAAAAGGCAG AGTACTCTGA GTGGCCAAAG TCCATGTTTA CTCAATCTGG    3360

CTCGGGCACT AAGCCTTGAA CCATATGACA CTGGTGCATG TGCCATCATC ATGCAGTAAT    3420

TTCATGGTAT ATCTTAATTA TATGGTTAAT AAAAAAAAGA TGGTGAGTGA ATAATGTGCG    3480
```

TGCATTCCTC CATGCACCAA TGGTGAATCT CTTTGCATAC ATAGAGATTC TGAATGATTA    3540

TAGTTTATGT TGTAGTGAAA TTAATTTTGA ATGTTGTTTT TAAATTTTAA TGTCACTTGG    3600

CTTGATTTAT GTTTTAACGA AGCTTATGTT ATGTATTTTA CTTTAATGAT ATTGCATGTA    3660

TTGTTAATTT AACATTGCTT GATCAGTATA CTCTTCTACT ATTAATTATA AATTGCACTG    3720

TTGTGTTTAA ACTTTTTACA AGTTAAGATA TATAATTATA AGTTTTAGTT CAATGTTAGT    3780

TATTCTTAAC TACATTTAAA CAAATTCCAC TTAAAGTTTT AATAAATAAT AACAAATAAT    3840

TATGGTAATA TAATACATTA AATGCAACAA AAAATGAAAT AAATAAAATA AAATAGCAAA    3900

TAATTGTTAT AATATTGTAA TATAATATGT ACCATATTCT TAACTGAAAT AGGGTCTAAC    3960

CTATAATCCC TAAA    3974

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:4:

GATGCATGGG CCCGAACATG GTGGAGCACG ACAC    34

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:5:

GCATATGATC ACATCAATCC ACTTGC    26

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:6:

CAGCGGTACC TCGAGCTGGT GGACTGACGC    30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:7:

CGGCCTCGAG GTACCTGAAG GAGCATGTTC    30

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:8:

```
GAGCTCCAGA CGTCTGGTGG ACTGACGCCA G                                    31
```

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:9:

```
CGGCGAGCTC GTGAAGGAGC ATGTTCGGC                                       29
```

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:10:

```
ATGCTGGTAC CTTTTTTTTT TTTTTT                                          26
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:11:

```
CCACGAGTCA CACGAATCGA                                                 20
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:12:

```
GGAGCACGAA GAGTACGAGA                                                 20
```

(2) INFORMATION FOR SEQ ID NO:13:

(i) SEQUENCE CHARACTERISTICS:

```
            (A) LENGTH: 17 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:13:

GAAGAGTACC ACGAATC                                                       17

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:14:

ATACCCGAGT ACAAGGAC                                                      18

(2) INFORMATION FOR SEQ ID NO:15:

(i) SEQUENCE CHARACTERISTICS:
            (A) LENGTH: 418 base pairs
            (B) TYPE: nucleic acid
            (C) STRANDEDNESS: double
            (D) TOPOLOGY: linear (ii) MOLECULE TYPE: Other Nucleic Acid (xi) SEQUENCE DESCRIPTION: SEQ ID NO:15:

CATATGGATT CTGGTTCGGC CCACCTCTGA AGGTTCCAGA ATCGATAGTG AATTCGTGGA         60

CACACAAATA CACGTTCTTT TCTTTCTATT TGATTAACCA TGGCTCATAG CATTCGTCAC        120

CCTTTCTTCC TTTTCCAACT TTTACTCATA AGTGTCTCAC TAGTGACCGG TAGCCACACT        180

GTTTCGGCAG CGGCTCGACG TTTATTCGAG ACACAAGCAA CCTCATCAGA GCTCCCACAA        240

TTGGCTTCAA AATACGAAAA GCACGAAGAG TCTGAATACG AAAAGCCAGA ATACAAACAG        300

CCAAAGTATC ACGAAGAGTA CTCAAAACTT GAGAAGCCTG AAATGCAAAA GGAGGAAAAA        360

CAAAAACCCT GCAAACAGCA TGAAGAGTAC CACGAGTCAC ACGAATCGAA TCGGATCC         418

(2) INFORMATION FOR SEQ ID NO:16:

(i) SEQUENCE CHARACTERISTICS:
            (A) LENGTH: 519 base pairs
            (B) TYPE: nucleic acid
            (C) STRANDEDNESS: double
            (D) TOPOLOGY: linear (ii) MOLECULE TYPE: Other Nucleic Acid (xi) SEQUENCE DESCRIPTION: SEQ ID NO:16:

CATATGGATT CTGGTTCGGC CCACCTCTGA AGGTTCCAGA ATCGATAGTG AGTTCGTGGA         60

CACAAAAATA CACTCAAAAT TCTTTTCTTT CTATTTGGTT AACCATGGCT CATAACTTTT        120

GTCATCCTTT CTTCCTTTTC CAACTTTTAC TCATTACTGT CTCACTAATA ATCGGTAGTC        180

ACACCGTCTC GTCAGCGGCT CGACATTTAT TCCAGACACA AACAACCTCA TCAGAGCTGC        240

CACAATTGGC TTCAAAATAC GAAAAGCACA AAGAGTCTGA ATACAAACAA CCAAAATATC        300

ACGAAAAGTA CCCAAAACAT GAGAAGCCTA AAATGCACAA GGAGGAAAAA CAAAAACCCT        360

GCAAACATCA TGAAGAGTAC CACGAGTCAC GCGAATCGAA GGAGCACGAA GAGTACGATA        420
```

```
AAGAAAAACC CGATTTCCCC AAATGGGAAA AGCCTAAAGA GCACAAGAAA CACGAAGTTG    480

AATATCCGAA AATACCCGAG TACAAGGACA ATCGGATCC                          519
```

FBLATE PROMOTER

FIELD OF THE INVENTION

The present invention relates in general to plant genetic engineering and in particular to the identification of the FbLate fiber-specific promoter and the use of this promoter to create novel genetically transformed cotton (Gossypium) plants and lines with varied cotton fiber characteristics and quality.

BACKGROUND OF THE INVENTION

Genetic Engineering of Plants

The hurdle of creating successful genetically engineered plants in major crop varieties is now being overcome sequentially on a plant-by-plant basis. While plant genetic engineering has been successfully demonstrated in several model plant species, most notably tobacco, carrot and petunia, these species are not considered agriculturally important. Therefore, researchers have directed their efforts toward improving commercially important crop plants through the use of genetic engineering (Potrykus, I., *Annu. Rev. Plant Physiol. Plant Mol. Biol.* 42:205–225, 1991).

The term "genetic engineering," as used herein, is meant to describe the manipulation of the genome of a plant, typically by the introduction of a foreign gene into the plant, or the modification of the genes of the plant, to increase or decrease the synthesis of gene products in the plant. Typically, genes are introduced into one or more plant cells which can be cultured into whole, sexually competent, viable plants which may be totally transformed or which may be chimeric, having some tissues transformed and some not. These plants can be self-pollinated or cross-pollinated with other plants of the same or compatible species so that the foreign gene or genes carried in the germ line can be bred into agriculturally useful plant varieties.

Current strategies directed toward the genetic engineering of plant lines typically involve two complementary processes. The first process involves the genetic transformation of one or more plant cells of a specifically characterized type. The term "transformation" as used herein means that a foreign gene, typically in the form of a genetic construction, is introduced into the genome of the individual plant cells. This introduction is typically through the aid of a vector, which is integrated into the genome of the plant. The second process then involves the regeneration of the transformed plant cells into whole sexually competent plants. Neither the transformation nor regeneration process need to be 100% successful, but must have a reasonable degree of reliability and reproducibility so that a reasonable percentage of the cells can be transformed and regenerated into whole plants.

Genetic Engineering of Cotton

Although successful transformation and regeneration techniques have been demonstrated in model plant species (Barton, et al., *Cell* 32:1033–1043 (1983), wherein the transformation and regeneration of tobacco plants was reported) similar results with cotton have only been achieved relatively recently. Umbeck, et al., *Bio/Technology* 5[3]:263–266 (1987); Firoozabady, et al., *Plant Mol. Bio.* 10:105–116 (1987); Finer, et al., *Plant Cell Rep.* 8:586–589, 1990; U.S. Pat. No. 5,004,863.

Successful transformation and regeneration of genetically engineered cotton plants has the potential to be of significant value to this agriculturally important crop. One of the most important benefits potentially achievable from genetically engineering cotton plants is the alteration and modification of cotton fiber quantity and quality.

Cotton Fiber

Cotton is one of the most important cash crops. Cotton fiber (seed hair) is a differentiated single epidermal cell of the ovule. At maturity the fiber cell consists of a cell lumen, primary cell-wall and secondary cell-wall. The primary cell-wall is made up of pectic compounds, cellulose, and small amounts of protein. The secondary cell-wall consists of cellulose. At maturity, the cotton fiber contains 87% cellulose.

Cotton fiber development can be divided into initiation, primary cell-wall synthesis, secondary cell-wall deposition, and maturation phases. Many hundreds of genes are required for the differentiation and development of cotton fiber. Work on in vitro translated fiber proteins (Delmer, et al., *J. Cell Sci. Suppl.* 2:33–50, 1985), and protein isolated from fiber (Graves and Stewart, *J. Exp. Bot.* 39:59–69, 1988) clearly suggests differential gene expression during various developmental stages of the cell. However, only a few of the genes involved in the biosynthesis of the large numbers of fiber-specific structural proteins, enzymes, polysaccharides, waxes or lignins have been identified (John and Crow, *Proc. Natl. Acad. Sci. USA* 89:5769–5773, 1992; John, *Plant Physiol.* 107:1477–1478, 1995). Since these genes and their interactions with environment determine the quality of fiber, their identification and characterization is considered to be an important aspect of cotton crop improvement.

The present invention is designed to approach fiber modification through genetic engineering. Such an endeavor requires fiber-specific promoters, genes that will modify fiber properties, and an efficient transformation technique.

The quality of the cotton fiber is dependent on such factors as the extent of elongation and degree of secondary wall deposition. It is assumed that a number of genes as well as environmental factors regulate the physical characteristics of the fiber, such as length, strength and micronaire value. However, the genes responsible for cellulose synthesis and fiber development in cotton plants are heretofore generally uncharacterized at a molecular level.

The most commercially useful plant fiber is derived from cotton (Gossypium arboreum, Gossypium herbaceum, Gossypium barbadense, and Gossypium hirsutum). However, there are other fiber-producing plants. These plants include the silk cotton tree (Kapok, Ceiba pentandra), desert willow, creosote bush, winterfat, balsa, rami, kenaf, hemp, roselle, jute, sisal abaca and flax.

Promoters

Promoters are DNA elements that direct the transcription of RNA in cells. Together with other regulatory elements that specify tissue and temporal specificity of gene expression, promoters control the development of organisms. Thus, there has been a concerted effort in identifying and isolating promoters from a wide variety of plants and animals.

Many promoters function properly in heterologous systems. For example, plant gene promoters such as rbcS, Cab, chalcone synthase and protease inhibitor from tobacco and Arabidopsis are functional in heterologous transgenic plants. (Reviewed by Denfey, et al., *Science* 244:174–181, 1989). Specific examples of transgenic plants include tissue-specific and developmentally regulated expression of soybean 7s seed storage protein gene in transgenic tobacco plants (Chen, et al., *EMBO J.* 7:297–302, 1988) and light-dependent organ-specific expression of Arabidopsis thaliana chlorophyll a/b binding protein gene promoter in transgenic tobacco (Ha and An, *Proc. Natl. Acad. Sci. USA* 85:8017–8021, 1988). Similarly, anaerobically inducible maize sucrose synthase-1 promoter activity was demonstrated in transgenic tobacco (Yang and Russell, *Proc. Natl. Acad. Sci. USA* 87:4144–4148, 1990). Tomato pollen promoters were found to direct tissue-specific and developmentally regulated gene expression in transgenic Arabidopsis and tobacco (Twell, et al., *Development* 109:705–713, 1990). Thus, some plant promoters can be utilized to express foreign proteins in plant tissues in a developmentally regulated fashion.

The art of plant biology lacks a promoter designed to specifically promote gene expression in late fiber development.

SUMMARY OF THE INVENTION

The present invention is a DNA sequence encoding an FbLate promoter. In one embodiment, the FbLate promoter is nucleotides 1 through 2315 of SEQ ID NO:3.

In another embodiment, the present invention is a gene construct comprising an FbLate promoter. Preferably, the gene construct also comprises a protein-encoding DNA sequence operably connected to the FbLate promoter. The protein-encoding DNA sequence is not natively connected to the FbLate promoter.

In another embodiment, the present invention is a method of obtaining an FbLate promoter. One first obtains genomic DNA from a fiber-producing plant and then screens this genomic DNA for sequences homologous to SEQ ID NOs:1 and 2 (FbLate cDNA sequences). One then examines the genomic DNA segments obtained for sequences upstream to the protein-encoding sequences and isolates the upstream sequences. These upstream sequences are then analyzed for the ability to preferentially promote gene expression in late fiber development.

In another embodiment, the present invention is a method of obtaining an FbLate promoter wherein one screens the genomic DNA described above with a probe prepared from SEQ ID NO:3 (genomic clone) to obtain sequences homologous to the specific FbLate promoter described herein.

The present invention is also a method of creating a transgenic fiber-producing plant cell. This method comprises the steps of constructing a plant expression vector that comprises a protein-encoding sequence and an FbLate promoter DNA sequence and introducing the expression vector into a fiber-producing plant cell.

Preferably, the fiber-producing plant cell is propagated into a fiber-producing plant and the protein-encoding sequence is expressed in the fiber cells of the fiber-producing plant.

The present invention is also a transgenic plant cell, plant and seed comprising a gene construct comprising an FbLate promoter. Preferably, the transgenic plant cell and plant is created by the method described above.

It is an object of the present invention to create a transgenic fiber-producing plant.

It is another object of the present invention to create a transgenic plant with altered fiber characteristics.

It is another object of the present invention to create a transgenic plant with altered fiber with improved strength, length or micronaire characteristics by using an FbLate promoter to promote expression of an advantageous gene during late fiber development.

It is another object of the present invention to provide a gene construct comprising an FbLate promoter.

It is another object of the present invention to provide a promoter that is most active at a particular developmental stage in fiber development.

It is another object of the present invention to create a transformed cotton plant with altered cotton fiber characteristics.

It is a feature of the present invention that the FbLate promoter may be truncated or modified and still retain promoter ability.

Other objects, features and advantages of the present invention will become apparent after review of the specification, claims and figures.

DETAILED DESCRIPTION OF THE INVENTION

Figure 1:
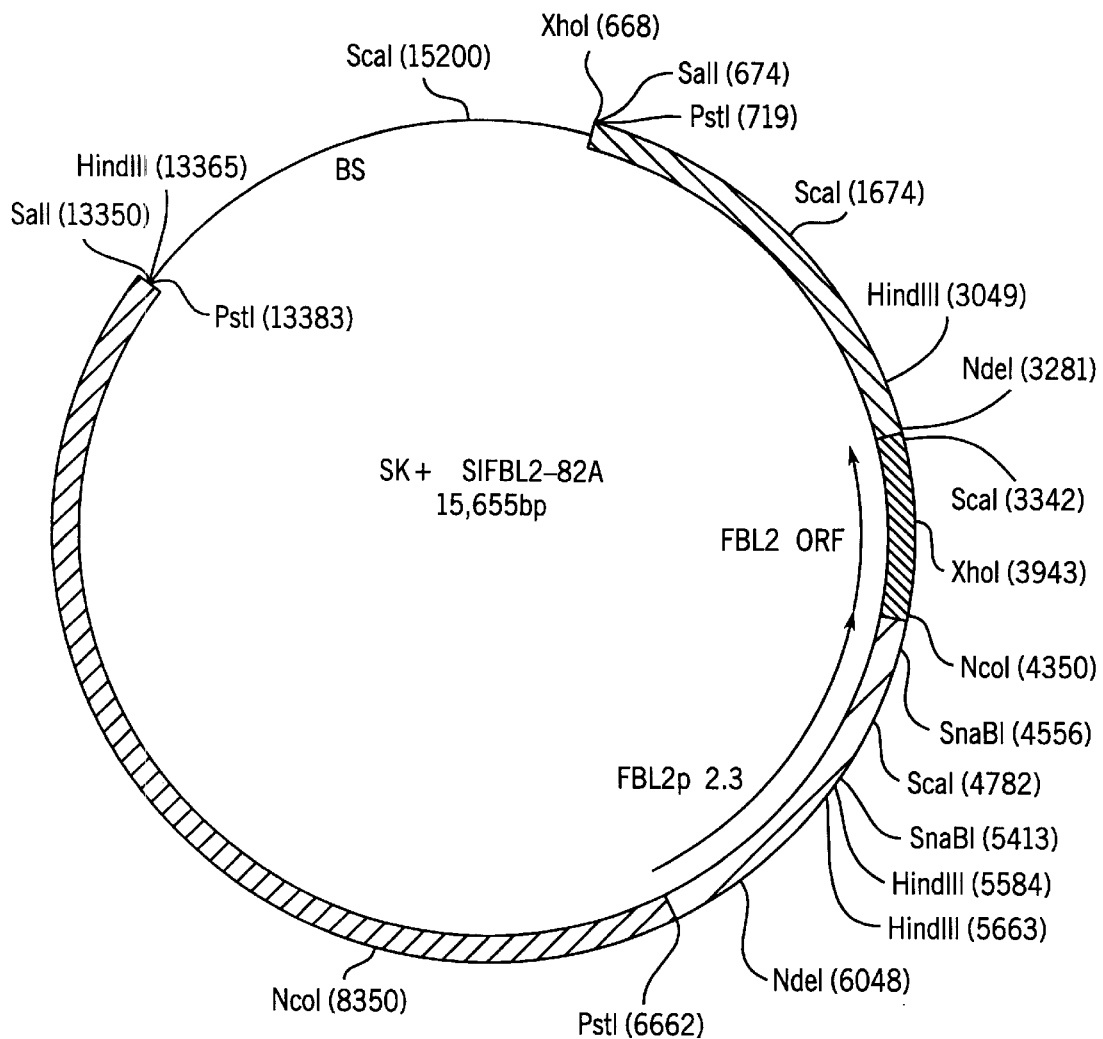
FIG. 1 is a diagram of the FbLate 2-82A gene.

In many instances, it is desirable for a transgene to be developmentally regulated so as to be expressed only in fiber cells at a proper developmental stage. This regulation can be most expeditiously accomplished by a promoter capable of preferential promotion. We are interested in expressing transgenes with a promoter that is active during late fiber development. We term such a promoter an "FbLate" promoter.

The present invention is a gene construct comprising an FbLate promoter and a method of creating transgenic fiber-producing plants, plant cells and seeds. Therefore, the method first involves identifying a promoter that preferentially promote gene expression in fiber cells during late fiber development (20 days post anthesis). (By "preferentially promote" we mean that the gene is either expressed only during late fiber development in fiber cells or is expressed more actively in fiber cells than it is expressed in other plant tissue cells.)

One way to identify suitable promoters is by isolating mRNA from fiber-producing cells, making a complementary DNA (cDNA) library of cDNA clones from the mRNA, and screening the cDNA library with cDNA generated from other tissues to identify and eliminate RNAs which are expressed in tissues other than those which produce fiber. This screening procedure will result in the identification of cDNA clones that are expressed preferentially in fiber cells. A similar process may be used to determine which cDNA clones encode RNA molecules that are prevalent in late fiber development.

After the identification process is complete, late fiber-specific cDNA clones may be used to screen genomic clones created from the DNA of fiber-producing plants. This screening process results in the selection of genomic clones with sequences homologous to the fiber-specific cDNAs. Because a FbLate fiber-specific promoter will be upstream from a sequence that is expressed specifically during late fiber development in a fiber cell, the promoter sequence may be identified on this genomic clone. These promoter sequences may be excised and attached to genes which if expressed in fiber cells would alter fiber quality or quantity. (Although the plant may be any of a number of varieties of fiber-producing plants, cotton, e.g., Gossypium plants, are the preferred plants for purpose of the present invention.)

To determine the sequences within a gene necessary for fiber-specific expression, nucleotide sequences of the coding region and regions flanking the coding region can be subjected to computer analysis to identify sequence patterns that correspond to consensus regulatory elements. Potential regulatory elements are usually present at the 5' flanking region of the gene, 30 to 100 bases upstream from the transcription start site in eukaryotic genes (for reviews see Breathnach and Chambon, *Annu. Rev. Biochem.* 50:349–383, 1981; Johnson and McKnight, *Annu. Rev. Biochem.* 58:799–839, 1989). In addition to the promoter (TATA box) other consensus sequences such as the CATC box and the CACA box, may also be present in specific groups of genes. Messing, J., et al., in *Genetic Engineering of Plants, an Agricultural Perspective,* Kosuge, et al. eds. pp. 211–227 (1983); Forde, B. G., et al., *Nucl. Acid Res.* 13:7327–7339 (1985); Goldberg, R. B., *Philos. Trans. Roy Sci. B*314:343–354 (1986). A search of the 5' flanking sequences of the gene can identify these sequence patterns.

The present invention is preferably performed with a cotton genomic DNA fragment that we have identified as containing FbLate promoter activity. Nucleotides 1 to 2315 of SEQ ID NO:3 represent the DNA sequences of the FbLate 2-82A promoter, one member of this gene family.

If one wishes to recreate the FbLate A promoter, one could first screen a cotton genomic library with a probe prepared from SEQ ID NO:3. One of skill in the art of molecular biology would be able to select a probe from this sequence, preferably nucleotide 2315 to nucleotide 3323, and screen a cotton genomic library to obtain homologous sequences. These sequences could then be analyzed for the presence for the FbLate A promoter sequence.

A sequence that is a variation of nucleotides 1 to 2315 of SEQ ID NO:3 may also contain promoter activity because it is not necessary for a DNA fragment to contain an identical nucleotide sequence to be functionally identical to the promoter sequences described herein. The sequence must only be sufficiently homologous to the fragment to retain promoter activity. Some nucleotide deletions, additions, and replacements, either naturally occurring or artificially induced, will have only a minor impact on gene expression.

A preferable sequence suitable as an FbLate promoter would be at least 80% homologous to nucleotides 1 to 2315 of SEQ ID NO:3. As experiments below demonstrate, a suitable FbLate promoter is preferably 2 kb in length. The FbLate promoter must be greater than the first 1.3 kb of SEQ ID NO:3 because this sequence is not sufficient for fiber-specific expression.

The promoter fragment described herein may be truncated to determine the smallest fragment capable of tissue-specific and development-specific expression. We refer to such a modification as a "functional deletion variation." Methods of truncating a clone include deleting sequences and digesting the clone with a restriction enzyme or other nuclease. These methods are commonly known in the art of molecular biology.

A suitable "functional deletion variation" of nucleotides 1 to 2315 of SEQ ID NO:3 will have the same promoter properties as the FbLate2-82A promoter described below. The description below demonstrate these properties.

One may use a transient reporter gene expression system to assess promoter activity of a specific portion of SEQ ID NO:3 or a test DNA fragment. In such an assay, the fragment to be assayed would be linked to a reporter gene and used to transform a plant cell. Useful reporter genes include chloramphenicol acetyltransferase (CAT), luciferase (Lux) and β-glucuronidase (GUS). Alam and Cook, *Anal. Biochem.* 188:245–254, 1990; Jefferson, *Plant Mol. Biol. Rep.* 5:387–405, 1987. We have described a reporter gene assay below.

Further confirmation of the promoter activity and tissue-specific and developmental expression can be obtained by stably integrating a chimeric construct comprised of the DNA segment and reporter gene into plants or animals and following the reporter gene's expression through development. Maximal expression of the RNA during the late fiber stage (20 days postanthesis) indicates that the test fragment is a suitable FbLate promoter. The Examples below describe a typical method of examining the expression of a specific RNA species.

Another way to obtain a sequence capable of preferentially promoting expression in fiber-producing plants is to probe a library of DNA obtained from a fiber-producing plant with a probe prepared from SEQ ID NOs:1–2 (late fiber cDNAs). The DNA probe does not have to encompass the entire sequence and only need be of a length sufficient to hybridize specifically to a suitable clone. If a sequence from an FbLate fiber-specific CDNA clone is used, one will isolate the genomic clone homologous to that cDNA. Because promoter sequences are found upstream from the sequences homologous to the CDNA clone, one must examine these upstream sequences to find the FbLate promoter. Analysis of the upstream sequence, as described above, will delineate which part of the sequence is needed for FbLate promoter activity.

After an FbLate fiber-specific promoter has been identified and isolated, the promoter must be placed upstream of a protein-encoding gene whose expression is desired. By "protein-encoding sequence" we mean a sequence that encodes at least a portion of a protein and is in either the sense or antisense orientation. By "expressed" we mean to include DNA sequences expressed as RNA or as protein. Preferably, the product of this gene is capable of altering fiber quality or quantity. Conventional molecular biological techniques may be used to create suitable constructs.

These constructs must be transformed into a cotton plant or cell. Stable integration and expression of foreign genes in cotton plants has been demonstrated and repeated. Umbeck, et al., *Bio/Technology* 5[3]:263–266 (1987); Firoozbady, et al., *Plant Mol. Biol.* 10:105–116 (1987). Using the techniques taught in these papers, the transformation of cotton tissues is accomplished by Agrobacterium infection and regeneration. Although a lengthy process, the Agrobacterium-mediated transformation of cotton has also been practiced by other laboratories and can now readily be replicated by those of ordinary skill in plant genetic engineering.

It is to be understood, however, that other methods for the transformation of cotton plants and lines are being studied, and that the transgenic cotton plants and lines with fiber genes introduced into them will prove advantageous and useful regardless of the method of transformation of the original tissues. Specifically, it has now been demonstrated that higher plants can be stably genetically transformed by particle-mediated transformation techniques, which avoid many of the difficulties and delays inherent in plant regeneration required by Agrobacterium plant transformation. McCabe, et al., *Bio/Technology* 6[8]:923–926 (1988).

Recent research results suggest that routine particle-mediated transformation of cotton is to be expected shortly.

The present invention is a useful genetic engineering tool for the introduction of altered fiber-specific characteristics into cotton plants. The identification and introduction of fiber-specific promoters from one cotton plant variety to another can be extended to include other exotic plants that produce fiber. Many of these plants will have fiber-specific promoters with one or more desirable qualities, which can be incorporated into a cotton plant.

The promoters of the present invention can be utilized in modulating the synthesis of fiber proteins or to introduce non-fiber proteins into fiber in a tissue-specific and development-specific manner.

Another approach to creating cotton plants with altered fiber characteristics is to create antisense genetic constructs with fiber-specific promoters to inhibit or induce the expression of one or more fiber genes in fiber cells. The theory behind antisense genetic constructs is that the production of RNA strands in the cells of an organism which are complementary to the mRNA of an endogenous gene will result in hybridization of the antisense RNA to the native mRNA resulting in decreased expression of the mRNA gene. Smith, et al., *Nature* 334:724–726, 1988; Bird, et al., *Bio/Technology* 9:635–639, 1991; Van der Krol, et al., *Gene* 72:45–50, 1988. Thus, in an antisense construct, a complete coding sequence for the mRNA is not needed. All that is needed is a sequence of sufficient length to construct a selectively hybridizing antisense RNA. Thus, the cDNA clones discussed below are of particular utility for this approach.

The following is a description of the process and materials used to identify a specific FbLate fiber-specific promoter (Fb-LateA) and to use the promoter to transform cotton plants. Although reference to cotton is specifically made, it is within the scope of the present invention to substitute other fiber-producing plants.

EXAMPLES

In General

Examples 1–2 describe the creation and analysis of fiber-specific cDNAs. Examples 3–8 describe the creation and analysis of FbLate cDNAs and promoters.

1. Isolation of RNA From Fiber

Fiber cells at different stages of development from fiber-producing plants were collected and quick-frozen in liquid nitrogen. Specifically, fiber cells from 15 and 23 day-old Coker 312 or 10 day-old Sea Island bolls were collected and quick-frozen. The frozen fiber cells were then powdered in a mortar in liquid nitrogen and homogenized in a homogenization buffer for 1.5 minutes using a polytron at full speed. The homogenization buffer included the following ingredients: 5 M Guanidine isothiocyanate; 0.2 M Tris-acetate (pH 8.5); 0.7% Beta-mercaptoethanol; 1% polyvinyl pyrrolidone (PVP, MW 40 Kd), and 0.62% sodium lauroyl sarcosine. Beta-mercaptoethanol and PVP were added just before use. A ratio of 1:2 of tissue (weight) to buffer (volume) was used.

The homogenate was filtered through Mira cloth and layered over a 1.5 ml pad of 5.7 M cesium chloride as described by Chirgwin, J. M., et al., *Biochemistry* 18:5294–5299 (1979). The homogenate was then centrifuged for 18 hours at 36,000 rpm in a SW 50.1 rotor at 20° C. After centrifugation, the RNA was collected as described by Chirgwin, et al. (supra).

The RNA was then further purified by phenol:chloroform extractions and precipitations in the presence of ammonium acetate as described for DNA by Crouse, et al., *Focus* 9[2]:3–5 (1987). Poly(A)+ RNA was obtained by oligo-(dT) chromatography as described by Maniatis, et al., in *Molecular Cloning: A Laboratory Manual*, Cold Spring Harbor Laboratory, Cold Spring Harbor, N.Y., (1982).

2. Library Construction and cDNA Clone Identification

Complementary DNA (cDNA) libraries were prepared from the mRNA according to the protocol developed by D'Alessio, et al., *Focus*, 9[1]:1–4 (1987) with the following exceptions: The first strand of cDNA was synthesized using a primer having the following sequence dATGCTGGTACC $(T)_{15}$ (SEQ ID NO:10); the second strand synthesis was carried out as described by D'Alessio, et al., supra, for tailing. The poly-(dC) tails were added to the double-stranded cDNA and then annealed to poly-(dG)-tailed psR322 plasmid vector (Bethesda Research Laboratories). The recombinant plasmids were used to transform *Escherichia coli* (*E. coli*) RR1 strain as described by Hanahan in *DNA Cloning a Practical Approach*, Vol. 1 (1985) pp. 109–135. The transformed cells were selected on agar plates containing the antibiotic tetracycline (12 mg/liter).

Separate cDNA libraries were constructed from the mRNAs from 10-day, 15-day, and 23-day-old fiber cells. For the 10-day fiber cell mRNAs, an oligo-(dT) primer was used for cDNA synthesis instead of the primer described above. The 10-day cells were selected to be representative of genes active during the primary cell wall stage of cell development. In the 15-day-old cell, both primary cell wall and secondary cell wall synthesis systems are active. The 23-day-old cells were selected to be representative of genes active principally during secondary wall synthesis.

The clones in the library were then transferred to nitrocellulose filters and duplicate filters were made according to Hanahan, et al., Gene 10:63–67 (1980). About 25,000 clones from the 15-day and 23-day libraries were screened using the following procedure. $^{32}$P-labelled single-stranded cDNA probes were prepared from poly(A)+RNAs using $^{32}$P-dCTP and reverse transcriptase as described by Maniatis, et al., supra. Probes were prepared from poly(A)+RNAs of 15-day, 23-day old fiber producing cells, and from 0-day ovule, leaf, root and flower cells. Prewashings, prehybridizations, hybridizations and washings of the filters were performed as described in detail in John, et al., *Proc. Natl. Acad. Sci. USA* 81:5628–5632 (1984).

The autographic signals from filters hybridized with $^{32}$P-labelled cDNAs from the different tissues were then compared. The clones which hybridized to cDNAs from fiber producing cells, but not to cDNAs from other tissues, were selected. The resulting clones were then subjected to a second cycle of differential screening as described above and additional clones were eliminated as non-fiber specific. This process was continued for a third and then a fourth time. This repetitive screening was to eliminate clones which showed hybridization to other than cDNAs from fiber producing cells.

The final collection of clones were then subjected to northern analysis. For this analysis, poly(A)+ RNA from different tissues were denatured in the presence of formaldehyde and size-fractionated on 1.5% agar/formaldehyde gels as described by John, et al., supra. The RNAs were then blotted to nitrocellulose and probed with $^{32}$P-labelled inserts of each individual clone. The clones that showed hybridization to only RNAs from fiber cells were selected. This screen resulted in the identification of cDNAs specific to five fiber specific genes. All manipulations on plasmid DNAs such as isolation, purification on cesium chloride gradients, restriction digestion, insert purifications by gel electrophoresis and electroelutions and $^{32}$P-labelling by nick-translations have been described previously (Maniatis, et al., supra and John, et al., supra).

The cDNA library from the 10-day old cells was then screened using a subtractive hybridization procedure as follows. The $^{32}$P-labelled cDNA from fiber was hybridized to excess biotinylated mRNA isolated from leaf tissue. The cDNA-biotinylated mRNA hybrids and the excess biotinylated mRNAs were separated from unhybridized cDNA by extraction with avidin in phenol:chloroform. The streptavidin was partitioned into the organic phase along with any biotinylated nucleic acid while the single-stranded cDNA remained in the aqueous phase. This procedure has been described elsewhere, Duguid, et al., *Proc. Natl. Acad. Sci. USA* 85:5738–5742 (1988).

Subtractive hybridization screening of 4788 clones of the 10-day cell library with leaf cDNAs resulted in 800 clones not present in the leaf. These clones were then screened by cDNAs generated from ovule, flower and root mRNAs. The results of this screening were 79 putative fiber-specific clones. The duplicate clones which hybridized to each other were detected by the procedure of polymerase chain reaction (PCR) (Saiki, et al., *Science* 239:487–491, 1988), Southern blotting and hybridization. The PCR reaction was carried out by first mixing 10 microliters of bacterial culture of the cDNA clone added to 90 microliters of distilled water. 20 microliters of that mixture was added to a PCR reaction buffer of 50 mM KCl, 10 mM Tris-HCl pH 8.0, 2.5 mM MgCl$_2$, 0.01% gelatin, 200 $\mu$M each of dATP, dCTP, dTTP and dGTP, 12.5 picomolar each of sense and antisense primers for pBR322, and 0.5 units of Taq polymerase. The final reaction volume was 52 microliters. The PCR reactions were carried out in a Perkin-Elmer-Cetus thermocycler.

The amplified DNA from the PCR reactions was separated by agarose gel electrophoresis and blotted onto nitrocellulose by the method of Southern, *J. Mol. Biol.* 98:503–517 (1975). One or more bacterial clones from the same group was amplified by the same procedure and the products also separated on agarose gel. The amplified insert DNAs were then excised from the gel and purified by electroelution. The purified DNAs, labelled with 32p by nick-translation, were hybridized with the Southern blot. Thus, the cross-hybridizing clones were identified in this fashion.

This procedure resulted in the identification of 19 putative fiber-specific clones. The clones were further analyzed by northern blots. Three of the clones were found to be fiber-specific. Another five of the clones were found to be differentially expressed to a higher degree in fiber and to a lesser degree in other tissues. Fiber-specific cDNA clones were then used as probes to screen genomic libraries and isolated cross-hybridizing genomic clones.

3. Characterization of FbLate-Specific cDNA clones

A 23-day fiber cDNA library was screened with cDNA from 24-day fiber poly(A) RNA. The first screen resulted in the identification of 573 hybridizing clones. The procedure was repeated with cDNAs from 23- and 10-day fiber poly (A) RNAs and resulted in the selection of 132 clones that showed strong hybridization to 23-day probe, but weak hybridization to 10-day probe. These clones were then subjected to cross hybridization to eliminate duplicate ones. Subsequently we hybridized the clones to 19 fiber specific cDNA clones identified from previous cDNA library screens (described above) to eliminate any previously identified clones. These 19 clones are described in U.S. Ser. No. 08/138,814 filed Oct. 18, 1993, M. John, (which is incorporated by reference). The cross-hybridizations eliminated a number of clones, and we selected 7 clones, (A8; A11; G4; G6; B2; C3; and F1) for further study.

Three of these clones (A8, A11 and G6) were then subjected to northern blot analyses to assess their expression patterns during development of the fiber. A8 and A11 clones strongly hybridized to 24-day fiber RNA while hybridization was weak or absent from 10-day fiber RNAs. Plasmid G6 hybridized to 24-day as well as 10-day fiber RNAs and also to leaf RNA.

The insert of A8 was sequenced and contains 974 bp (SEQ ID NO:1). The 645 bp insert of clone A11 was sequenced and is described at SEQ ID NO:2. This clone will be referred to as FbLate-2. We refer to clone A8 as FbLate-1. The nucleotide sequences of FbLate-1 and FbLate-2 were compared using the Bestfit computer program of Genetics Computer Group Inc. (GCG) Madison. The sequences showed a 90% similarity, suggesting that these two mRNAs are members of one gene family. The longest open reading frame in FbLate-1 cDNA is 621 bases while FbLate-2 had an open reading frame of 425 bases.

4. Preparation of Genomic DNA and Genomic Clones

Genomic DNA from Sea Island cotton, was prepared according to the methods described in *Current Protocols in Molecular Biology*, (Eds. Ausbel, F. M., et al.) Wiley, (1987), pp. 2.3.1–2.3.3, with the following modification: The frozen plant material was homogenized in extraction buffer containing 1% polyvinyl pyrrolidone. The purified genomic DNA was digested with restriction endonucleases and transferred to nitrocellulose filters by the Southern blotting technique. Southern, supra.

The filters were then probed with nick-translated inserts of the fiber-specific CDNA clones previously identified. The hybridization and blot washing conditions are described in John, et al. (supra). The Southern hybridization results showed that each of the cDNA clones hybridized to only a few (one or two) bands in the genomic DNA. This result indicates that there are only one or two genes corresponding to these cDNAs in the cotton genome.

A Sea Island cotton library was prepared by Clonetec, Inc., of California, in EMBL-3 or lambda DASH vectors. For the preparation of the library, the DNA was partially digested with Mbo I. 8–22 Kb DNA fragments were cloned into the Bam HI site of the vector. Inserts 10–15 Kb were present in the phages. The inserts were excised by either Sal I for EMBL-3 and lambda DASH or Eco R1 for lambda DASH. The genomic libraries were plated on *E. coli* NM 538 as described in *Current Protocols in Molecular Biology*, (supra).

The genomic library was screened with $^{32}$P-labelled FbLate-2 cDNA after transferring the library to nitrocellulose filters according to the methods described in *Current Protocols* (supra) and John, et al. (supra). By this method, genomic clones containing sequences homologous to the fiber-specific cDNA clones were isolated.

The primary screen resulted in the identification of 27 hybridizing phages. A second round of screening eliminated 24 of these while a third screen resulted in the identification and isolation of one phage (EMBL-SI82A). EMBL-SI82A contained a 12.7 kb insert which was excised by restriction digestion with Sal I. The insert was then cloned into Sal I site of Bluescript SK+ vector to generate pSKSIFbLate2-82A clone. The insert was then characterized by restriction digestion with various enzymes followed by Southern blot analysis.

Subcloning of genomic DNA inserts into plasmid or phagemid vectors was done using standard protocols. Ligated DNAs were transformed into *Escherichia coli* strain XL-1 Blue (Stratagene). Recombinant clones were selected on the basis of blue/white selection on X-gal, IPTG (5-bromo-4-chloro-3-indoyl-beta-D-galactophyranoside; isopropyl-beta-thio-galactophyranoside) plates. The plasmid sizes of the recombinant clones were then analyzed by SDS-agarose gel electrophoresis (Sekar, V., *Biotechniques* 5:11–13, (1987)). The inserts of the clones were further characterized by restriction mapping and Southern analysis. *Current Protocols in Molecular Biology* (supra). If necessary, further subcloning of smaller restriction fragments that contain the cDNA hybridizing regions was also undertaken. The above protocols enable one to determine the approximate boundaries of a given gene.

The nucleotide sequence of the gene and the corresponding cDNAs may be analyzed by computer programs to determine, among other things, the tentative coding region, presence of introns and exons, 5' and 3' noncoding regions and putative promoter regions. The software that we have used for this purpose is that of Genetics Computer Group (GCG), Madison. Once the detailed sequence analysis was performed and various putative structural components of the gene were identified, we were able to confirm these findings by various experiments. For example, we used a chimeric marker gene construct that includes the promoter fragment to transform a test cell. By observing the presence or absence of the marker enzyme activity, one can analyze the promoter activity of that DNA fragment.

5. Characterization of genomic clones

The DNA insert in pSKSIFbLate2-82A was characterized by restriction analysis and Southern blot hybridization. This process resulted in the identification of a 1.5 kb Sca I fragment that hybridized strongly to the FbLate-2 cDNA. In addition there were two other fragments, a 4 kb Nco I fragment and 800 bp Sca I fragment that showed weak hybridization. Based on the cDNA sequence, the 4 kb Nco I fragment is likely to contain the 5'-end of the gene along with the promoter. FIG. 1 shows the restriction map of pSKSIFbLate2-82A. Based on the hybridization pattern, it appeared that the FbLate-2 gene is localized within a 6.3 kb region flanked by Nco I and Sca I sites. In order to locate the gene more precisely, we used primers based on the FbLate-2 cDNA to sequence the gene.

The nucleotide sequence of a 3974 bp region of pSKSIFbLate2-82A clone was determined and is shown in SEQ ID NO:3. (We shall refer to the clone described above as the FbLate2-82A gene.) Comparison of the FbLate2-82A gene sequence with that of FbLate-1 and FbLate-2 cDNA sequences showed that both cDNAs were homologous to the gene. In case of FbLate-1 cDNA, the sequence similarity was 92.4% while that of FbLate-2 was 98.9%. A comparison of the nucleotide sequence of the FbLate2-82A gene with those available in the GenBank data bank showed that the gene is not homologous to any other sequences. The comparison was carried out using GCG program FASTA in December 1993. Small regions of similarities were found with a number of genes. Examples are 52.4% similarity in a 430 bp region of the *C. elegans* mitochondrial genome and a 59.6% similarity to a 350 bp region of *P. falciparum* rhoptry associated protein 1.

The FbLate2-82A gene sequence had a long open reading frame spanning 4061 bases. An ATG initiation codon was present at position 2315. In order to determine the location of the start codon of the FbLate2-82A gene, we undertook cloning of the remaining piece of the FbLate-2cDNA by a modified polymerase chain reaction, the rapid amplification of cDNAs (RACE; Saiki, et al., *Science* 239:487–491, 1988; Frohman, et al., *Proc. Natl. Acad. Sci. USA* 85:8998–9002, 1998)

As described below, the FbLate-2 cDNA is a partial clone of 645 bp. Based on the northern analysis, the FbLate-2 transcript is about 1300 bases long. Thus, it appears that about 650 bases of the 5'-end of this clone was missing. In order to clone the missing 5'-end we used "RACE," which is a PCR protocol that generates cDNAs by amplifying copies of the region between a single point in the transcript and the 5'-end. Two primers based on the sequence of cDNA clone All were synthesized (SEQ ID NOs:11 and 12) and used to PCR-amplify the 5'-end of the FbLate-2 mRNA. We used a RACE kit from Clontech Lab. (Palo Alto, Calif.). The kit contained an AmpliFinder anchor and AmpliFinder anchor primer that are necessary to complete the reaction. Detailed protocal of RACE is described in *PCR protocols, A guide to methods and applications*, Eds. Innis, M. A.; Gelfand, D. H. ; Sninski, J. J.; and White, T. J., Academic Press, NY, pp. 28–38, 1990, as well as instructions from the kit supplier.

The insert from one of the clones (519 bp) was then sequenced (SEQ ID NO:16) and compared to the sequence the genomic clone, FbLate2-82A. The clone showed a 91.6% similarity at the nucleotide level. The homology of the RACE product started from nucleotide position 2269 of the FbLate2-82A gene. At position 2315 of the gene there was an ATG initiation codon.

A second RACE product was also generated using primers based on the sequence of cDNA clone A8. We used two primers (SEQ ID NO:13 and SEQ ID NO:14) and generated an insert of 420 bp (SEQ ID NO:15). The sequence of the second race clone also was determined and compared to that of the FbLate2-82A gene. The nucleotide comparison showed 91.7% similarity. Moreover, the homology started at position 2269. These findings implicate that the FbLate-2 mRNA is transcribed from the region of the 2269 nucleotide. The ATG at position 2315 is likely to be the initiation codon.

When the nucleotide sequence was translated into protein starting with the ATG at 2315, a 354 amino acid protein sequence was derived. The protein had a calculated molecular mass of 43.4 kDa with an isoelectric point of 5.97. Predominant amino acid residues of the protein were glutamic acid (26.3 mole %) and lysine (18.9 mole %). Assessment of the hydrophilicity showed the protein to be hydrophilic. There was a small hydrophobic region at the N-terminus, but otherwise the protein is hydrophilic in nature.

A computer search of the nucleotide derived amino acid sequence of FbLate2-82A gene with the available protein sequences in the data bank revealed no significant homology with any of the proteins as of April 1995. Based on these analyses we conclude that the gene we described here has not been identified from other organisms. The function of the gene is not known.

6. Determination of Promoter Activity

A chimeric gene construct was made using the putative promoter and the reporter gene beta-glucuronidase (GUS) of *E. coli*. GUS catalyzes the cleavage of 5-bromo-4-chloro-3-indoyl glucuronide (X-Gluc). The indole derivative produced by this cleavage undergoes oxidative dimerization to form a blue dye. Cells that produce this blue dye can be detected easily. The GUS marker system has been described in detail by Jefferson, et al., in *Proc. Natl. Acad. Sci. USA* 83:8447–8451 (1986) and in *Plant Mol. Biol. Rep.* 5:387–405 (1987). The GUS gene is publicly available (ATCC Accession No. 67641).

Chimeric plasmids were constructed by ligating a promoter-less GUS coding region along with a transcription termination signal Nos(A) at the 3'-end into a vector cassette as a Nco I/Sal I fragment. An AMV 5' untranslated leader is added to the 5'-end of the GUS gene as a Nco I/Xho I fragment. This construct (p2117, FIG. 2) contains unique Xho I and Nco I sites for introducing putative promoters.

If a cauliflower mosaic virus 35s (CaMV 35s) promoter is ligated into Xho I or Nco I site and the resulting plasmid (p2119) is introduced into plant cells by particle acceleration, GUS expression can be detected. Ellis, et al., *Plant. Mol. Biol.* 17:19–27, 1991. We have tested GUS expression by histochemical staining as well as quantitative measurements (Jefferson, R. A., supra). If the construct containing an unknown DNA is found to be active in expressing GUS, then it can be concluded that the DNA fragment contains a promoter that directs the expression of GUS gene.

The assay involves transforming a test cotton tissue, such as hypocotyl, with different plasmids. We transformed the hypocotyl tissue via a particle-mediated transformation method disclosed in U.S. Pat. No. 5,015,580, hereby incorporated by reference.

Using the Bluescript subclone and exonuclease/mung bean deletion procedure in which a series of clones with differing lengths of the 5' fragment are generated, one can identify minimum lengths of 5' DNA necessary to express the gene in fiber cells. These types of procedures will enable one to identify promoters from all genomic clones. Based on this knowledge, one can construct various developmentally regulated expression vectors containing fiber genes of interest and introduce them into plants.

We analyzed our reporter gene constructs in two ways, through histochemical staining and through fluorogenic analysis. The histochemical staining gave a quick "yes or no" answer while the fluorogenic analysis provided quantitative data.

a. Histochemical Staining

Histochemical localization of beta-glucuronidase activity in plant tissues is achieved by incubating freshly cut, transformed tissue sections in a solution containing 5-bromo-4-chloro-3-indoyl glucuronide (X-Gluc). X-Gluc is prepared by dissolving 5 mg of X-Gluc in 50 µl of dimethyl formamide and diluting it to 10 ml with 50 mM sodium phosphate buffer pH 7.0. After staining (1–3 hours at 37° C.), the tissue sections were rinsed off with 70% ethanol. Cells containing an active GUS gene turn blue.

b. Fluorogenic Assay

The quantitative assay for GUS activity depends on the cleavage of 4-methyl umbelliferyl glucuronide (MUG) by the GUS enzyme into a fluorogenic product 4-methyl umbelliferone (MU). MU is fluorescent when its hydroxyl group is ionized. (Jefferson, R. A., supra). The fluorogenic assay is carried out as follows. Plant tissue was homogenized in extraction buffer (50 mM $NaH_2PO_4$, pH 7.0, 10 mM EDTA, 0.1% Triton X-100, 0.1% sodium lauroyl sarcosine, 10 mM β-mercaptoethanol). We included proteinase inhibitor PMSF at a final concentration of 20 µg/ml and 1% insoluble PVP. The extract, after centrifugation (300 µl) was added to 1 ml of MUG buffer. The MUG buffer is made up of 1 mM MUG in the above extraction buffer. The mixture is incubated at 37° C. and at time points 0, 20, 40, and 60 minutes an aliquot (100 µl) is withdrawn and added to 1 ml stop solution (0.2 M $Na_2CO_3$). The fluorescence at each time point is measured in a fluorocalorimeter (excitation at 365 nm, emission at 455 nm). Protein concentration of the plant extract is determined by Bradford assay using a test kit from Bio-Rad Laboratories (M. Bradford, *Anal. Biochem.* 72:248–254, 1976). The fluorimeter is calibrated with freshly prepared MU standards. The results are given as pmole MU/mg/min.

The above system for the detection of promoters, namely transient expression of chimeric GUS plasmids introduced into hypocotyl tissues through particle bombardment, appears to be limited in that no tissue specificity of expression is observed for any of the promoters tested. Thus, promoters (LAT 52, Cab) that were proven to be tissue-specific in heterologous stable transgenic plants (Twell, et al., *Mol. Gen. Genet.* 217:240–245 (1989); Ha and An, *Proc. Natl. Acad. Sci. USA* 85:8017–8021 (1988)) are found to express GUS transiently when introduced into cotton hypocotyls by particle bombardment.

Figure 2:
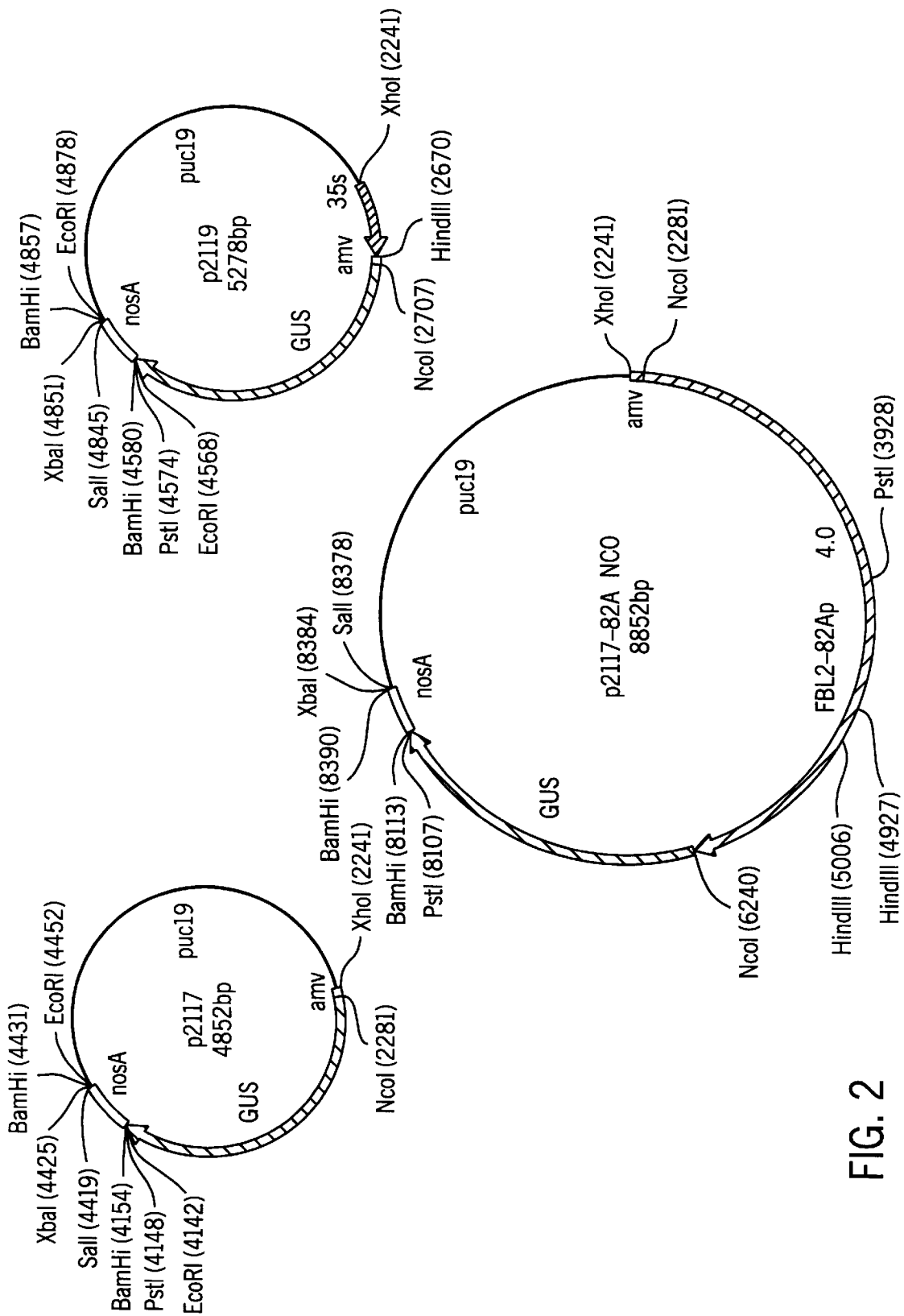
FIG. 2 is a diagram of plasmids useful for an assay to determine promoter function.

The following control experiments were conducted along with each of the promoter assays. FIG. 2 describes plasmids useful in this assay.

1. Plasmid p2117 was introduced into cotton or soybean hypocotyl tissues as a negative control. Because p2117 contains a promoter-less GUS gene, no GUS activity should be detected.

2. The tissue was bombarded with p2119. p2119 contains a GUS gene driven by 35s promoter. This is a positive control, for GUS should always be expressed.

3. The DNA fragment being tested for activity is introduced into hypocotyl tissue. This is to demonstrate that the fragment in question has no GUS-like activity.

7. Identification of specific FbLate-2 promoter termed "FbLate2-82A promoter."

FbLate2-82A gene contains an Nco I site at postion 2315 near the ATG initiation codon. It is likely that the 5' region from the ATG would contain the promoter of the gene. The gene was digested with Nco I and a 4 kb DNA fragment upstream of the ATG was isolated.

The 4 kb Nco I fragment (see FIG. 3) was subcloned as described above into a plasmid (p2117) containing a promoter-less GUS gene at the Nco I site. A clone containing the insert in the correct orientation was selected by restriction digestion analysis and is referred to as p2117-82ANco. Plasmid DNA from p2117-82ANco was then subjected to Transient GUS expression assay system as described above. Cotton seed axes were bombarded with p2117-82ANco, p2117, p2119 and pSKSIFbL2-82A. FIG. 2 shows the restriction maps of p2117, p2119 and p2117-82ANco. The seed axes were then subjected to histochemical detection of GUS activity. Plasmids p2117-82ANco and p2119 showed blue staining indicating GUS expression, while as expected p2117 and pFblate2-82A showed no GUS activity. These results indicate that the 4 kb Nco fragment contains a promoter.

In order to further reduce the size of the fragment containing the promoter, we assembled two more constructs as follows. The 4 kb Nco fragment was restricted with Pst I to generate a 2.3 kb Nco/Pst I fragment and cloned into PGEM 5Z vector. The insert was then excised as a Sal/Nco fragment, the Sal site originating from the vector. The 2.3 kb Sal/Nco fragment was then cloned into Xho/Nco site of p2117 to test for transient GUS activity.

The 2.3 kb Nco/Pst fragment was shown to direct expression of GUS in cotton seed axes. These results indicate that the promoter of FbLate2-82A gene is located within the 2.3 kb Nco/Pst I fragment. We refer to this promoter as FbLate2-82A promoter.

Further deletion of the 2.3 kb fragment to a 1.3 kb fragment was done as follows. The GUS coding region along with Nos poly(A) was added to an SK+ plasmid as a Hind III/Xba fragment. The SK+ vector containing GUS gene was then digested with Hind III/Nco I to remove the AMV leader sequence. Subsequently the pGEM 5Z vector containing the 2.3 kb Nco/Pst fragment was digested with Hind III/Nco to isolate a 1.3 kb FbLate 2 promoter fragment. This fragment was then ligated into the Hind/Nco site of the GUS containing SK+ vector and tested for GUS expression by bombardment into cotton seed axes.

Figure 3:
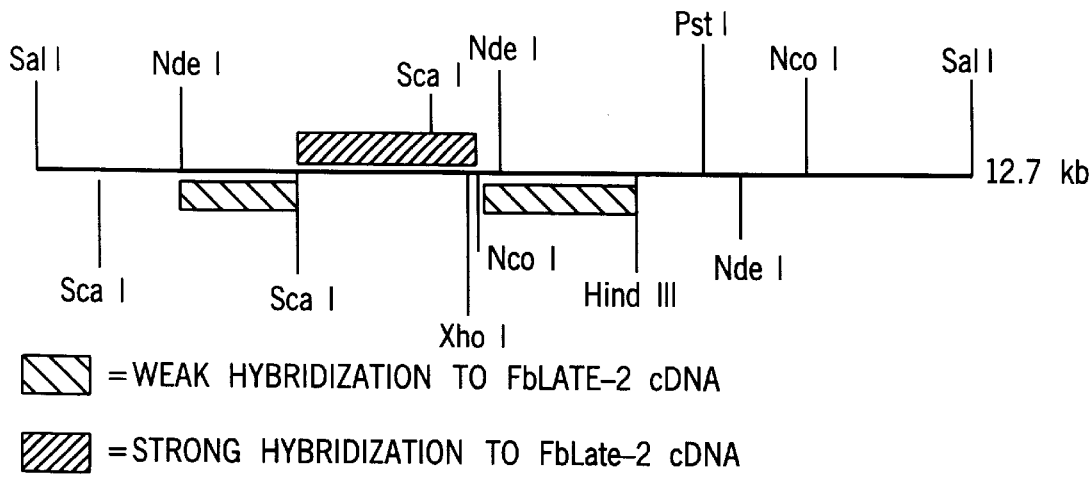
FIG. 3 is a diagram of promoter fragments contained within the pSKSIFbLate2-82A plasmid.
Figure 3:
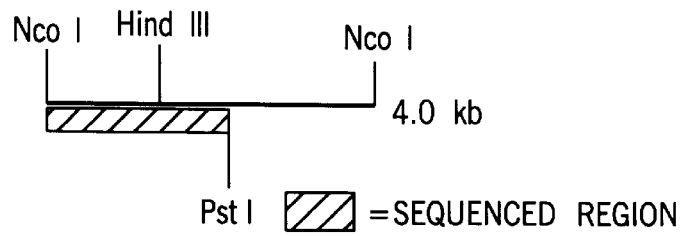
Figure 3:
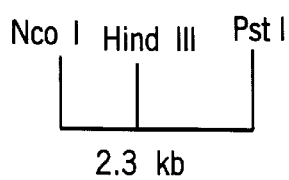
Figure 3:
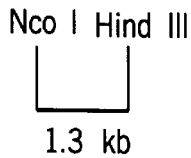

The 1.3 kb promoter fragment was also found to direct transient expression of GUS indicating that the promoter is located within the 1.3 kb fragment. FIG. 3 shows the restriction sites of the 3 promoter fragments described above.

However, it is necessary to test these various fragments in stable transgenic plants to confirm their promoter activities along with tissue and developmental expression.

8. Testing of FbLate2-82A gene promoter activity in stable transgenic plants a. In General The final test of promoter activity and its tissue and developmentally regulated expression was accomplished by integrating the promoter fused to a gene into the plant genome. In this instance, we chose to link the putative FbLate2-82A promoter with two genes coding for enzymes in the pathway for the synthesize of a biopolymer, polyhydroxy butyrate(PHB). Presence of PHB in fiber has the potential to modify fiber properties such as dye binding, thermal properties and absorbency.

Poly-beta-hydroxybutyric acid (PHB) is a form of PHA found as an intracellular storage compound in many species of bacteria. PHB was identified in *Bacillus megaterium* in 1925. (Lemoigne, M., *Ann. Inst. Pasteur. Paris.* 35:144, 1925). PHB is a biodegradable thermoplastic that serves as a carbon and energy source for the bacterium. Due to its high degree of crystallinity, PHB is hard and brittle. Holmes, et al., U.S. Pat. No. 4,393,167, discusses the use of PHB and PHB blends.

In many bacteria, PHB is synthesized via a three-step metabolic pathway in which the enzymes ketothiolase, NADP-dependent acetoacetyl-CoA reductase, and PHB synthase (PHB polymerase) catalyze the conversion of acetyl CoA to PHB (Dawes and Senior, *Adv. Microb. Physiol.* 10:135–266, 1973). The genes corresponding to these three enzymes have been cloned from *Alcaligenes eutrophus*. *E. coli* can be made to synthesize PHB after transformation with these genes (Slater, et al., *J. Bacteriol.* 170:4431–4436, 1988; Schubert, et al., *J. Bacteriol.* 170:5837–5847, 1988; Slater, et al., *Applied and Environmental Microbiology* 58:1089–1094, 1992; Peoples and Sinskey, *J. Biol. Chem.* 264:15298–15303, 1989; Peoples and Sinskey, *J. Biol. Chem.* 264:15293–15297, 1989).

b. Cloning of Acetoacetyl CoA reductase and PHB synthase

Acetoacetyl CoA Reductase

The DNA sequence of acetoacetyl CoA reductase gene was reported in Peoples and Sinskey, J. Biol. Chem. 264:15293–15297, 1989 and in U.S. application Ser. No. 08/241,943, filed May 12, 1994, inventor M. John (both hereby incorporated by reference). The reductase gene was cloned by PCR amplification from A. eutrophus using MEJ76 and MEJ77. MEJ76 contains a Bam HI site and MEJ77 contains a Xba I site. This amplification created a 741 bp fragment that was cloned into Bam HI/Xba I sites of SK+ vector. This resulting plasmid is referred to as PHB-B. The coding sequence of the Acetoacetyl CoA Reductase gene can be taken from Peoples and Sinskey (supra).

The PCR product of acetoacetyl CoA reductase was sequenced and compared with the published sequence. Four nucleotide changes were observed. Starting from the initiation codon, nucleotide "A" at position 433 was changed to nucleotide G. This would result in an amino acid change from lysine to arginine. A second change was detected at position 497 where a C was changed to a T in the PCR product. This will cause an amino acid sequence change from alanine to valine in the PCR product. Further, at position 556 nucleotide "A" was changed to a G. At position 557, a T was changed to C. These two changes result in a change of amino acid from isoleucine to alanine.

In order to test whether the PCR-produced acetoacetyl CoA reductase gene could be translated into a product with the correct molecular size, we conducted the transcription/translation-coupled reticulocyte lysate experiment. A protein of 27 kDa was obtained. The size of this product agrees with the know molecular weight of this enzyme.

The enzymatic activity of the acetoacetyl reductase gene was tested in the transcription/translation coupled in vitro system (supra). No activity was detected. The gene was excised by digestion with Bam HI/Xba I and treated with Klenow polymerase to blunt the ends. Bam HI linkers were then added. The gene was then cloned into expression vector, DR 540 as a Bam HI fragment and orientation determined by restriction map analysis. Cells containing either sense or antisense plasmids exhibited no reductase activity after IPTG induction. Thus, it is apparent that the substitutions in the gene may have caused the loss of enzymatic activity of the protein. Therefore, we repeated the PCR cloning of reductase under PCR conditions to increase the fidelity of the system (Innis and Gelfand in PCR Protocols, Eds. M. A. Innis, D. H. Gelfand, J. J. Sninsky, T. J. White; pp. 1–12, 1990). Primers MEJ76 and MEJ305 and a second set of primers, MEJ76 and MEJ304 were used along with 50 micromolar dNTPs, 0.5 unit of Taq polymerase and 5 μl of bacterial culture. Other conditions were similar to those described earlier (supra). MEJ304 and MEJ305 contain Bam HI sites. MEJ305 primes at the stop codon of the reductase gene while MEJ304 primes 99 bases downstream of the stop codon. Hence, the PC product of MEJ76/305 will have only the coding region of reductase and is referred to as PHB-Bs, while the PCR product of MEJ76/304 will result in coding region and 99 bases of 3' untranslated region. The longer insert is referred to as PHB-B1.

The PCR products after Bam HI digestion were cloned into Bam HI sites of SK+ vector. After determination of orientations we conducted transcription/translation reactions with the genes in the SK+ vector. Both PHB-Bs and PHB-B1 were found to express active enzyme. We also cloned the PHB-B1 and PHB-Bs inserts into DR540. Cells containing sense orientation of the genes exhibited reductase activity while those with antisense genes showed no activity.

From these experiments we conclude that substitutions at nucleotide positions 433, 497, 556, 557 are detrimental to the activity of the reductase gene.

PHB Synthase (PHB Polymerase) Gene

The DNA sequence of the PHB synthase gene is reported in Peoples and Sinskey, *J. Biol. Chem.* 264:15298–15303, 1989 and in U.S. Ser. No. 08/241,943, filed May 12, 1994, inventor M. John (both hereby incorporated by reference). The 1770 bp polymerase gene was cloned by PCR amplification from A. eutrophus. Four PCR primers, MEJ70–73 were used. PCR amplification using primers MEJ70 and 71 resulted in a 580 bp fragment while MEJ72 and 73 gave a 1200 bp fragment. The 580 bp fragment was digested with Eco RI/Bam HI and cloned into SK vector. This fragment contains an internal Bgl II site. The 1200 bp fragment as well as the SK vector containing the 580 bp fragment was then digested with Bal II and Bam HI and the 1200 bp fragment was ligated to Bal II/Bam HI sites. The orientation of the fragment in relation to the 580 bp 5'-end was determined and clones containing the correct orientation were selected. This clone will be referred to as PHB-CL.

The PHB synthase PCR product was sequenced and compared to published sequence (Peoples and Sinskey, supra, 1989. There were two nucleotide substitutions. First one was at position 103, counting from the initiation codon, where a T was substituted by a C. This substitution results in an amino acid change from serine to proline. The second substitution was at 1533 where a T was substituted by a G. This will not cause a change in amino acid composition.

In order to correct the mutation at position 103, we repeated PCR amplification of the 580 bp fragment using MEJ70/71 under more stringent PCR conditions (supra). The fragment was digested with Eco RI and Nco I. This resulted in a 250 bp fragment that was cloned into Nco/Eco RI sites of SK+ vector and sequenced. We selected clones that showed no changes at position 103 or elsewhere and excised the insert by digesting with Nco/RI. Plasmid PHB-C1 was digested with Nco/RI and the large DNA fragment was gel purified. The above 250 bp fragment was then ligated to PHB-C1.

The translation product of PHB synthase gene was examined in a transcription/translation-coupled reticulocyte lysate system. The reaction product was found to be 64 kDa, which is in agreement with the known molecular weight of PHB synthase.

c. Transformation

1. In General

We chose to use accelerated particles to transform cotton with the DNA constructs. A style of apparatus for accelerating such particles has been described in detail in U.S. Pat. No. 5,015,580 (hereby incorporated by reference). In brief, small metal particles are coated with nucleic acid material and accelerated into target cells. By an unknown mechanism, a certain percentage of the target cells will incorporate the nucleic acid.

Other particle acceleration apparatus, such as the commercially available BioRad (Biolistics) PDS-2000 particle acceleration instrument, will be suitable for the present invention. Other non-accelerated particle methods are also suitable. Such methods include electroporation, viral vectors, and Agrobacterium-mediated transformation.

Stable integration and expression of foreign genes in cotton plants has been demonstrated and repeated. Umbeck, et al., *Bio/Technology* 5[3]:263–266 (1987); Firoozabady, et al., *Plant Mol. Biol.* 10:105–116 (1987). In each of these references, the transformation of cotton tissues is accomplished by Agrobacterium infection and regeneration. Although a lengthy process, the Agrobacterium-mediated transformation of cotton has also been practiced by other laboratories and can now readily be replicated by those of ordinary skill in plant genetic engineering.

It is to be understood, however, that new methods for the transformation of cotton plants and lines are being studied, and that the transgenic cotton plants and lines with the promoters of the present invention will prove advantageous and useful regardless of the method of transformation of the original tissues. The description below suggests a preferable method of transformation.

2. Surface Sterilization

We have developed a cotton transformation system that is particularly advantageous for the practice of the present invention. The process begins with commercial cotton seed, which must be sterilized. In our example, we used DP-50 cotton seeds, although other varieties would be equally suitable. We chose DP-50 because it is a cotton variety with good growing characteristics but a coarse fiber.

A sieve beaker system is autoclaved. A sieve beaker system is a beaker with dozens of holes drilled in its bottom that can be nested inside a non-drilled glass beaker. It is also useful to utilize a third sterile beaker for rinsing the seeds so that the sieve beaker can be rested in the sterile beaker while discarding wash water.

The sieve beaker is filled with cotton seeds. The beaker into which the sieve beaker is nested is then filled with a mixture of 50% Chlorox bleach so as to cover the seeds. The seeds are allowed to rest within the bleach solution for three minutes. The bleach is drained and the seeds are then rinsed five times with distilled water.

The surface sterilized cotton seeds are then placed in a sterile glass beaker. A cotton antibiotic sterilization medium is added to the beaker at twice as much volume as there are seeds, This medium consists of sterile distilled water to which has been added carbenicillin at 200 mg per liter, cefotaxime at 125 mg per liter, and 30 mg each of BRAVO WP, BENLATE 50 DF, and CAPTAN 50 WP per liter. The seeds are incubated in the sterilization medium for three to four hours in the dark at room temperature.

Then the seeds are drained by pipette. The beaker is refilled with fresh cotton antibiotic sterilization medium and the seeds are incubated for an additional three hours.

The seeds were then drained and incubated overnight at 15° C. in the dark to germinate. If germination proceeds appropriately, the seed germination could be stopped by refrigeration at 4° C., for up to three days following the germination process.

3. Seed Dissection

After the germination of the seeds, or the removal of the germinated seeds from storage, seeds are selected that are just beginning to germinate. Overly germinated or ungerminated seeds are discarded. The proper stage of germination is defined as fully imbibed seeds with one to four millimeters of the radicle exposed. Under sterile conditions, the seed axis is removed out of the seed. This is done by manual manipulation with gloved hands to remove the seed axis from both of its cotyledons and its seed coat. The process is relatively easy to perform with practice. It is possible to readily develop the ability to pop the seed coat axis apart from the seed, without damaging the seed axis, or leaving any of the cotyledon on the seed axis.

The excised seed axis is then washed in three to four rinses of sterile distilled water. The washed but undissected explants are either dissected immediately or stored by plating on standard OR ccb medium made with fresh benzylaminopurine or BAP, but no NAA. This media is described by Barwhale, et al., *Planta*, 167:473–481 (1986), but without the NAA hormone. The explants are plated on the agar surface by being laid on their side. The excised embryonic seed axis plated on the agar medium are incubated at 15° C. in the dark overnight.

4. Exposing The Meristem

The washed seed axis explants are now ready for micro dissection to expose the meristems of the seed axes. This dissection is performed under sterile distilled water and with sterile tools. The dissection consists of removing the embryonic leaf, or leaves if there is more than one, that obscure the meristem on each of the excised seed axes. The fully dissected explants are transferred to another petri dish containing sterile distilled water.

5. Pre-Blast Hormone Treatment

After all the dissections are completed, the explants are again washed in three to five rinses of sterile distilled water. The free water is removed by pipette after the final rinse. The treated explants are then laid on their side on the surface of standard OR ccb medium made with fresh BAP but not NAA. The explants are incubated overnight, or for 24 hours maximum, at 15° C. in the dark. The treated excised embryonic axes with exposed meristems are now ready for the accelerated particle transformation blast.

6. Genetic Material And Carrier Particle Preparation

Ten milligrams of amorphous crystalline gold powder, or of an equal mixture of 1–3 micron gold spheres and crystalline gold powder is measured into the bottom of a 1.5 ml Eppendorf microfuge tube. Care is taken to ensure that the gold did not spill on the sides of the tube, since that would make it difficult to resuspend the gold due to the small volumes used in the preparation process. 100 µl of 0.1 M spermidine (free base) is added to this microfuge tube and the microfuge tube is vortexed well. 1 to 20.0 µg of double-stranded DNA is then added to the microfuge tube and the tube is then vortexed gently but completely. While the DNA/carrier particle mixture is gently vortexed, 100 µl of 2.5 M $CaCl_2$ is added to the tube. The vortex is stopped, and precipitation is permitted for 10 minutes at room temperature. The preparation could be stored at this point for some time. Shortly before use, the mixture of DNA and carrier particles is given a brief spin in a microfuge. The cleared supernatant is removed completely, and the precipitant consisting of the DNA and carrier particles is resuspended in 20 ml of 100% ethanol. The resuspended DNA and carrier particle mixture is then sonicated in a water bath sonicator for two to three brief one second exposures. The resulting suspension is then coated onto the carrier sheet, at a calculated rate of 0.05 milligrams per square centimeter of the carrier sheet. After allowing the gold to settle, the excess ethanol is drained away and the sheet is dried. These preparations of DNA and carrier beads are made fresh daily.

7. Blasting

At this point in the process, the carrier sheets are placed upon the apparatus for the blasting process. This procedure and apparatus are similar to that disclosed in U.S. Pat. No. 5,015,580, which is hereby incorporated by reference. The cotton explants are plated on 12% xanthin gum target plates. Using the normal germination and pre-blast hormone treatments described above, typically 25 explants are found to fit on each of the target surface within the blast area.

The parameters used for the particle-mediated transformation blast itself includes a relatively high electric discharge voltage through the gun, typically in the range of 15–25 kilovolts. The standard voltage used is 18 KV. The voltage is adjusted to achieve a level of impact on the treated axes such that the rate of survival of the meristems is between 40% and 90%. In other words, the blast force is adjusted to a level such that at least some of the meristems are rendered non-viable by the process. The blasting experiments are conducted at 350 ml of mercury, with helium introduced at a rate of 1.5 L per minute at atmospheric levels, and approximately 5.0 L per minute under the vacuum.

Each of the target tissues is blasted once or twice during the same day. Target tissues blasted twice in the same day are blasted once in the morning and once in the afternoon, with the explants stored between successive blasting procedures in a moist chamber at approximately 28° C. in the dark. The target tissues are placed in the dark immediately after each blasting exposure.

8. Post-Blast Protocol

The explants are now removed from the target surface, and plated in a normal orientation on OR ccb medium made with fresh BAP but no NAA. Care is taken not to expose the explants to excessive light. Care is taken to keep the meristem from contact with any media, and no wet plates are utilized. The fresh explants are plated and then incubated at 28° C. in the dark for one to two full days.

One day after the blasting, a preliminary assessment of transient enzyme activity is conducted on the resultant tissues. The assay is conducted at this time to check for the quality of the bead preparation protocol, and also to look specifically at the number of transformation events in the meristem, a rough approximation of which can be made by checking the transient activity of the explants at this stage. Although-due to the heavy damage from the blasting process 20% to 60% of the meristems are sufficiently damaged so as to never produce shoot, those same damaged meristems will, upon assay, exhibit excellent transient gene activity particularly of the GUS gene using this procedure. Thus, the tissues can be assayed at this step for the percentage of GUS activity, even though shoots are not yet evident on the meristems subjected to the procedure.

Following the initial post-blast incubation on the medium described above, the cotton explants are transferred to the dextrose-based woody plant medium (WPM), minus BAP plus carbenicillin and benoxyl, in plantcons again under low light. The WPM medium mixture, based on Lloyd and McCown, Proc. International Plant Propagation Soc. 30:421–427 (1981) is prepared as follows: $NH_4NO_3$ (400 mg/L), $Ca(NO_3)_2.4HOH$ (556 mg/L), $K_2SO_4$ (990 mg/L), $CaCl_2.2HOH$ (96 mg/L), $KH_2PO_4$ (170 mg/L), $H_3BO_3$ (6.2 mg/L), $Na_2MOO_4.2HOH$ (0.25 mg/L), $ZnSO_4.7HOH$ (8.6 mg/L), $CuSO_4.5HOH$ (0.025 mg/L), $FeSO_4.7HOH$ (27.8 mg/L), $Na_2EDTA$ (37.3 mg/L), Thiamine.HCL (1.0 mg/L), Nicotinic acid (0.5 mg/L), Pyridoxine.HCl (0.5 mg/L), Glycine (2.0 mg/L), Myo-inositol (100 mg/L), Dextrose (20 g/L), Agar (3.0 g/L), Gelrite (1.1 g/L), Calcium gluconate (1.29 g/L), Carbenicillin (200 mg/L) and Benoxyl (60 mg/L). The tissues are incubated at 28° C. in the dark for one to seven days.

Following the culturing steps outlined above, the plantcons are then moved to full light exposure so as to induce shoot development in the tissues under cultivation.

9. Identification of Transformant Events

Particle bombardment-mediated cotton transformation leads to two types of transformation events, epidermal and germline (McCabe and Martinell, 11:596–598, 1993). In the epidermal (or non-germline) transformants, only the epidermal layer of cells are transformed. Thus the progeny of the epidermal transformant are not transgenic. During the screening of the putative transgenics, the epidermal transformants are distinguished by histochemical staining of leaf petiole, where only the epidermal layer would stain for GUS. Epidermal transgenics are propagated through cuttings. Since cotton fiber originates from the epidermal layer of the plant, these transformants are suitable for testing the effect of transgenes on fiber modification.

The second type of transformation event produces a germline plant. In germline transformants the transgene is passed on to the progeny in a Mendelian fashion (McCabe and Matinell, Bio/Technology 11:596–598, 1993). Germline transformants are detected by histochemical staining of leaf petiole, where peidermal and vascular tissues show GUS staining. For fiber modification, both types of transformants are useful.

The plantcons containing bombarded tissue are then moved to a cultivation chamber and exposed to 16 hour light periods at 28° C. A number of cultured explants then proceed to exhibit shoot elongation and development from the plated tissues. It then becomes necessary to evaluate the growing shoots to ascertain the level of germ line transformation events which are achieved through this process. The assay procedure is conducted at such a point that the shoots each have developed their first leaves. The outermost one-third to one-half of each leaf is then cut off completely across the leaf through the midrib. The leaves are then assayed for GUS activity to identify GUS-positive expressing plants.

At this point, the quality of the event is characterized depending on the level of GUS activity in the leaf. Some of the leaves exhibited only uneven or irregular GUS expression, indicating chimeric plants. Based on the results below and experience with other plant systems, we have observed and verified that a transformation of the vascular system, as exemplified by the leaf petiole, correlates very well with the occurrence of a germline transformation event. Some of the leaves seemed to be totally blue, indicating putatively clonal transgenic plants. If the plant is characterized as germline transformed, the plant is transferred into rooting conditions and grown out in the greenhouse. For chimeric plants, the plant is pruned to just above the transformed leaf so as to force the axillary bud to grow from the transformed area of the plant after which it is retested.

For plants that tested negative, the leaves are removed, and the plants are cultured until newly formed leaves are regenerated. Tests are again conducted. This process is repeated three times before a final negative determination for the plants is made.

The entire process as described above, from initial plating of the seeds to the recovery of an initial generation transgenic plant requires approximately three to five weeks. Based on the initial results as described above, we expect that approximately one mericlonal transgenic plant will occur per approximately 100 to 500 meristems exposed to the blasting process. Of the mericlonal plants produced from the process, approximately 0.1%–1.0% will be found to have transformed germ lines. Thus, although the yield may seem low, this process allows for the relatively rapid and more inexpensive generation of large numbers of transgenic plants than other procedures because the process can be performed quickly. The transgenic plants will transmit the inserted genes by Mendelian inheritance, and the process can be performed directly on elite cotton lines, even Sea Island and Pima lines, which are resistant to tissue-culture methods.

d. Construction of expression vector

A general expression vector with a marker gene for cloning different genes was constructed as follows. A Bluescript SK+ plasmid was modified by introducing a new Nde site in the fi phage intergenic region. The SK+ vector was digested with Nae and phosphorylated Nde linkers were ligated to the Nae site. Clones that were linearized upon Nde digestion were selected. The addition of Nde site to the fi region may have disabled the single-strand-forming ability of the phagemid.

A GUS marker gene driven by constitute 35S promoter (Cauliflower mosaic virus 35s) was excised from plasmid p2119 by digesting with Sal I/Xho I. A 1.8 kb DNA fragment was gel-purified and treated with T4 polymerase to blunt the ends. Nde linkers were then added and ligated into the Nde site of modified SK+ vector. Clone carrying the 1.8 kb GUS gene were then selected by gel electrophoresis and restriction digestion pattern analysis.

Figure 4:
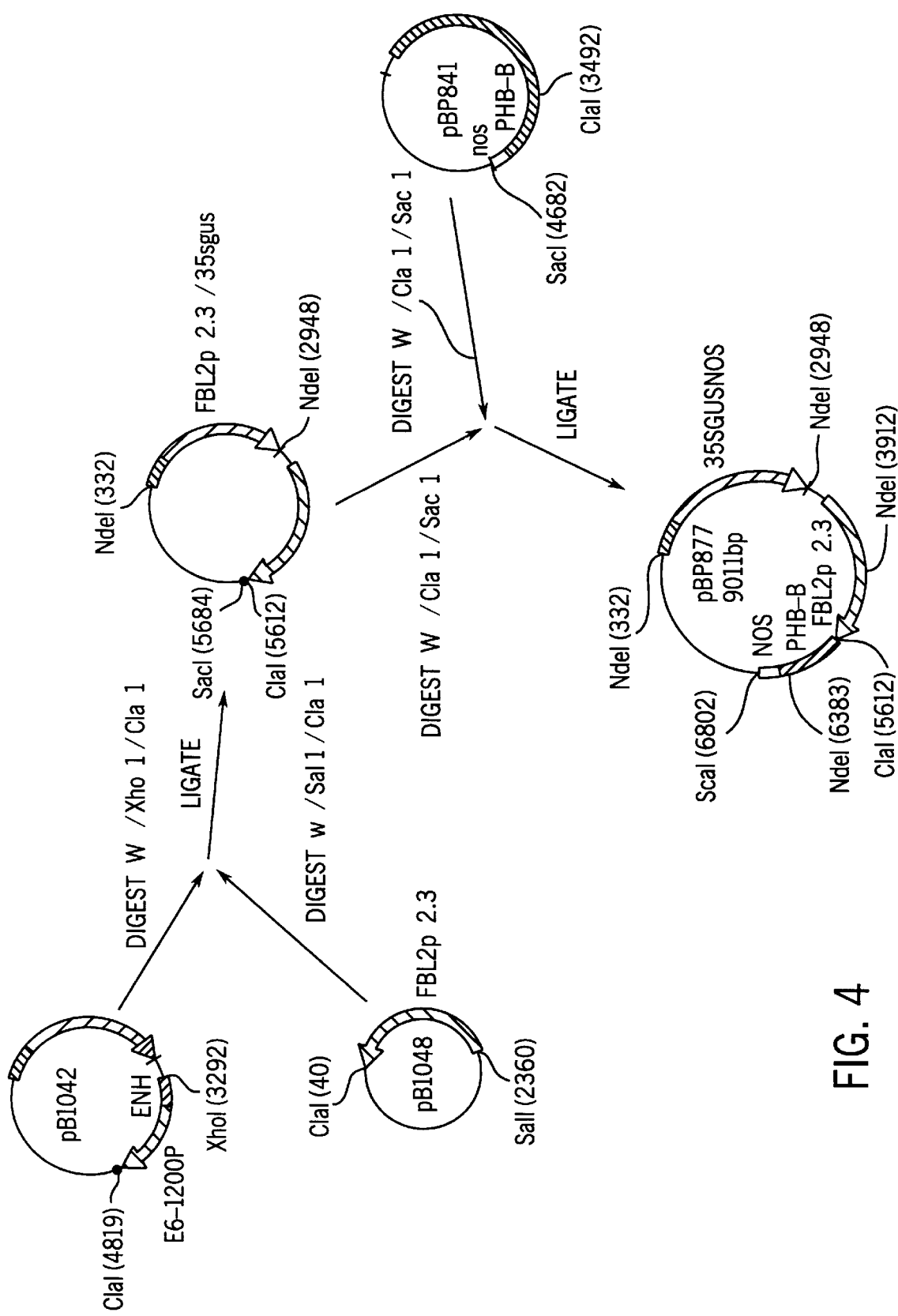
FIG. 4 is a diagram of the construction of plasmid BP877.

Next the FbLate2-82A promoter was modified and added to the expression vector as follows. The 2.3 kb DNA fragment contains the 5' untranslated leader sequence of the gene. It also contains the translational initiation (ATG) codon. Any gene linked to the downstream of the promoter may have its own translation initiation codon. Thus in order to prevent initiation from the FbLate2-82A start site we removed the ATG from the 2.3 kb fragment by treating it with mung bean nuclease. The 2.3 kb FbLate2-82A promoter in pGEM 5Z (see above) was linearized at Nco I site and treated with mung bean nuclease to remove the ATG codon. Cla linkers were then added to the blunt end site and ligated. Several clones were tested for the presence of a new Cla I site. DNA from one of the positive clones [pB1048] was sequenced to confirm the deletion of the ATG codon. The modified promoter fragment is excised from the pB1048 by digestion with Cla/Sal I and cloned into the Xho/Cla site of pB1042 (FIG. 5) to form plasmid FBL2P2.3/35SGUS. Next an acetoacetyl Co A reductase gene along with Nos poly(A) addition signal from pBP841 was added to the above vector at Sac/Cla site to complete the expression vector construction. (pBP841 is an expression vector containing acetoacetyl CoA reductase gene.) This plasmid is referred to as pBP877. FIG. 4 shows the construction of pBP877.

A second construct with a smaller size promoter fragment and two elements that are designed to increase the strength of the promoter was generated. We deleted about 1.0 kb from the 2.3 kb FbLate2-82A promoter. This was accomplished by digesting the 2.3 kb fragment-containing plasmid, pB1048, with Pst/Hind III and religating the plasmid after T4 polymerase treatment. Clones containing a 1.3 kb promoter fragment were selected by gel electrophoresis and restriction mapping. This clone is referred to as pFBL2P1.3* ATG/GEM.

A number of DNA elements are known to increase expression of genes in plants. We added two such elements to the short FbLate2-82A gene promoter—a transcription enhancer and a second element that reduces the position effect, scaffold attachment region (SAR; Breyne, et al., Transgenic Res. 3:195–202, 1994).

Figure 5:
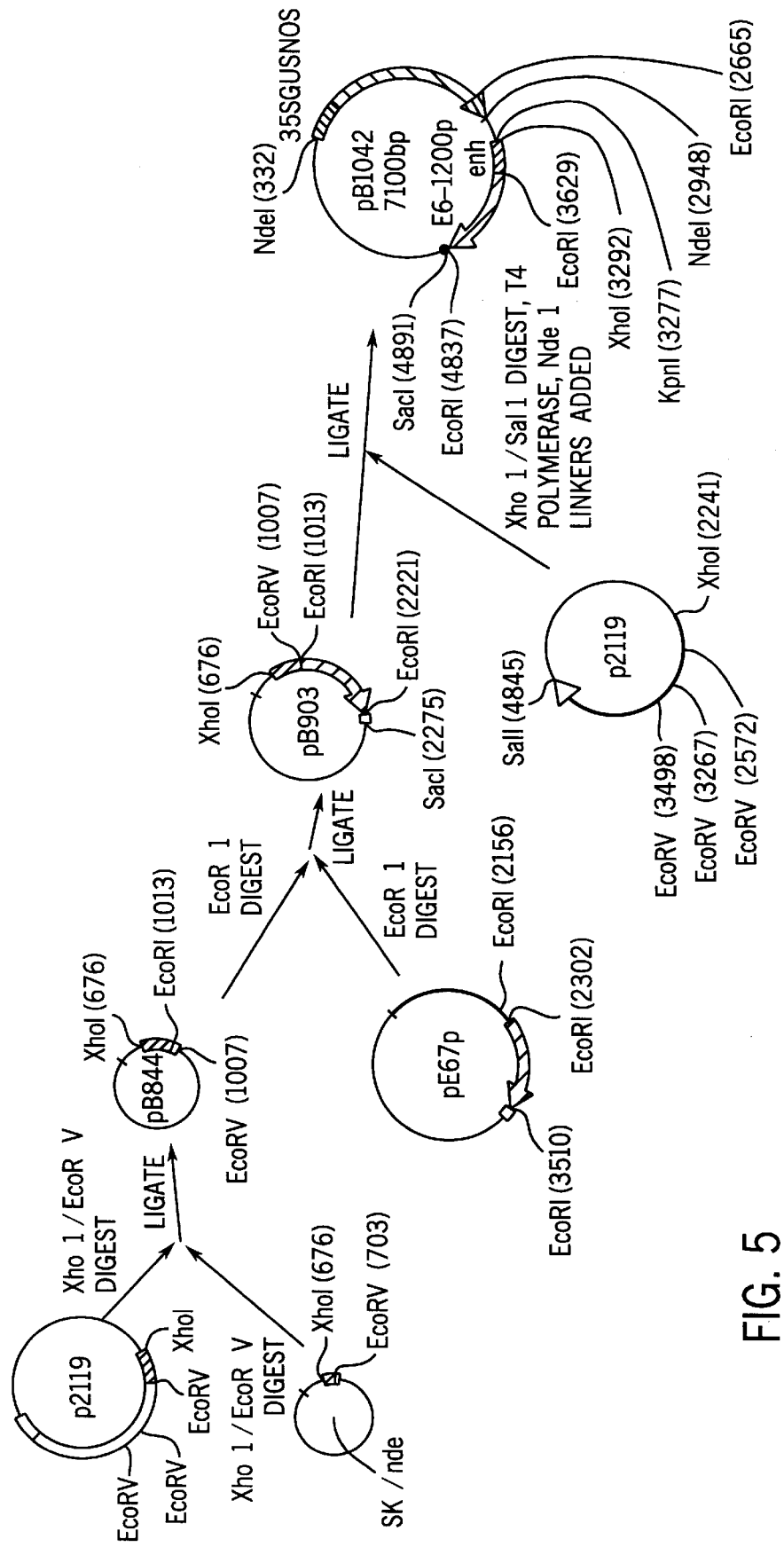
FIG. 5 is a diagram of the construction of plasmid B1042.

The following section describes cloning of these two elements. First, a plasmid vector containing enhancer and SAR was constructed. This vector contained a fiber promoter E6, that can be replaced by other fiber promoters. The E6-promoter is described in U.S. Ser. No. 08/138,814 filed Oct. 18, 1993, M. John, et al., hereby incorporated by reference. The 35S enhancer element was PCR amplified from plasmid p2119 using oligos MEJ 574 and 575 (SEQ ID NOs:4 and 5, respectively). The PCR product was then cloned into pT7 Blue vector (Novagen, Madison) to generate pT7-EN. The enhancer element from pT7-EN can be excised by Nde I/Nsi I. The 35S enhancer (330 bp) can also be obtained from P2119 by digestion with Xho/Eco RV and cloned into modified SK+ vector to generate pB844. A short E6 promoter with ATG codon deleted (1.2 kb, called E6-7P) was excised from plasmid pSKSIE6-3B as an Eco RI fragment and ligated into pB844 to generate pB903. The marker gene GUS was then added at the Nde site to generate pB1042. FIG. 5 describes the construction of pB1042. The promoter in pB1042 can be replaced by other promoters to construct various expression vectors.

The transgene expression in transgenic plants are known to be influenced by the position of gene integration in the genome. This apparently results in wide variation of transgene expression levels. In our hands generally only one or two cotton plants out of five express the transgene at high enough levels necessary for detection by enzymatic assays. In recent times a number of investigators have shown that including a DNA element found in yeast genome, the scaffold attachment region (SAR), resulted in the reduction of "position" effect. In few cases there was also an increase in expression levels of the transgene when the gene was flanked by SAR elements (Breyne, et al., supra, 1994; Georgiev, et al., Eur. J. Biochem. 200:613–624, 1991; Schoffl, et al., Transgenic Res. 2:93–100, 1993).

In order to test whether SAR would decrease the position effect, we cloned the SAR element from yeast DNA and included two of them in our FbLate2-82A promoter construct. The 800 bp SAR element was PCR amplified using oligomers, MEJ 466 & 467 (SEQ ID NOs:6 and 7) that contained Kpn sites. A second pair of oligomers, MEJ 468 and 469 (SEQ ID NOs:8 and 9) containing Sac sites were also used. The amplified DNAs were then cloned into the Kpn and Sac sites of SK+ vectors. The SAR/K n element will be linked to the 5'-end of the promoter, while the SAR/Sac element would be used to the 3'-end of the gene. The partial sequence of the cloned SAR elements were obtained to verify the identity of the cloned DNAs. The SAR elements were moved into promoter vector pB1042 (see description above). The Kpn/SAR element was ligated to the Kpn site to generate pB1045 and the Sac/SAR element was added to pB1045 to generate pB1049. Plasmid pB1049 contained the E6 promoter. pB1049 was linearized at BstXI and after treatment with T4 polymerase a Nos (A) fragment was added to generate pB1071. The E6 promoter in p1071 can be replaced by other promoters to generate constructs containing various promoters, enhancer and SAR elements.

Figure 6:
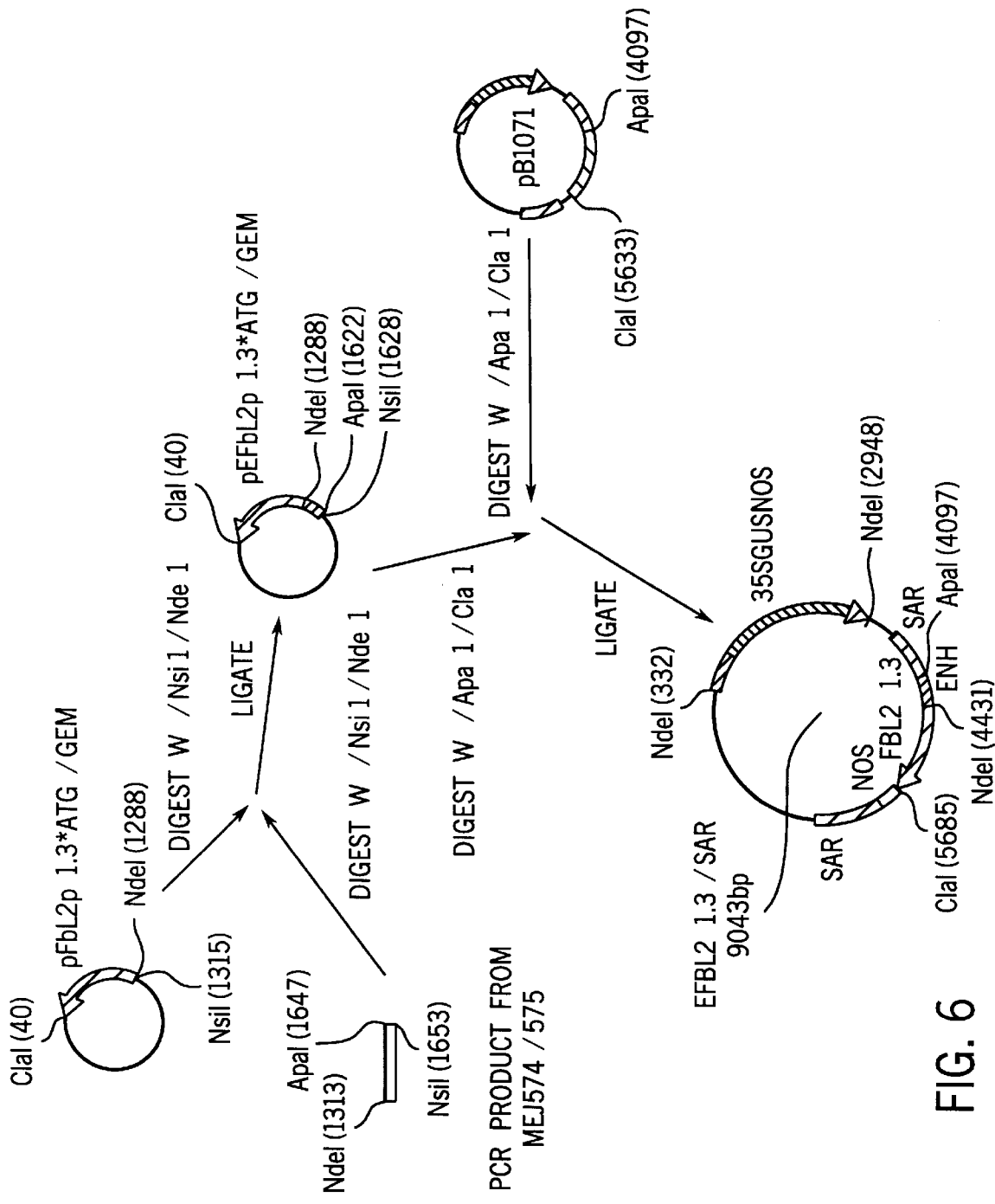
FIG. 6 is a diagram of the construction of plasmid EFBL2 1.3/SAR.

The 35S enhancer was excised by digesting the plasmid pT7-EN with Nsi/Nde. The purified fragment was then cloned into pFBL2P1.3* ATG/GEM vector containing the 1.3 kb FbLate2-82A promoter at Nsi/Nde sites to generate pEFBL2P1.3* ATG/GEM. The promoter element along with the enhancer can now be excised from the plasmid by digesting it with Apa/Cla. Plasmid EFBL2P1.3* ATG/GEM was digested with Apa/Cla I and the promoter along with the enhancer element was gel purified. The SAR vector pB1071 plasmid was digested with Apa/Cla to remove the E6 promoter. The gel purified vector was then ligated with the 1.3 kb Ava/Cla fragment of FbLate 2-82A. This resulted in a 1.3 kb FbLate2-82A promoter with enhancer and SAR elements. The resulting plasmid is referred to as pEFBL21.3/SAR. Construction of the above plasmids is shown in FIG. 6.

Figure 7:
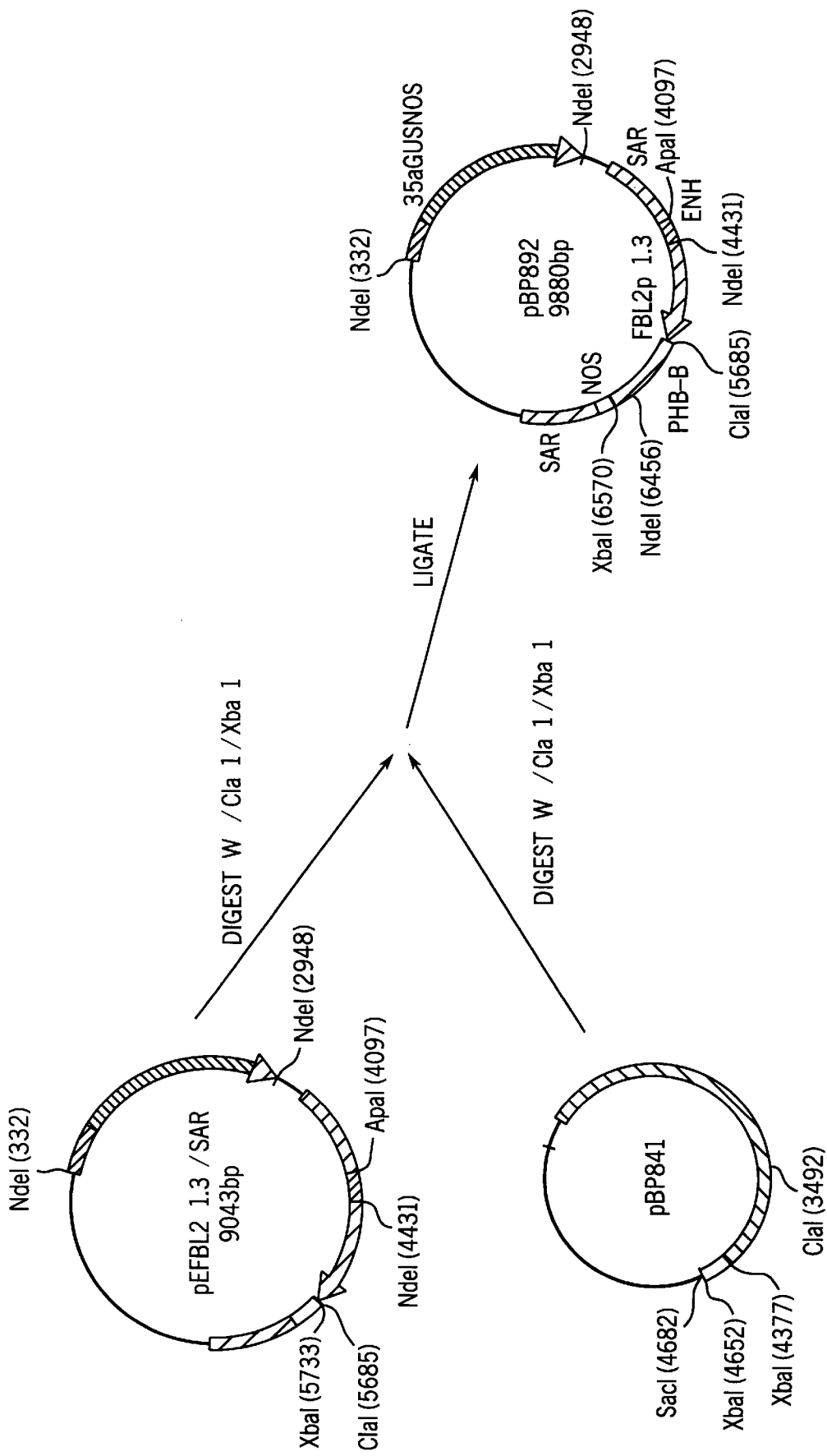
FIG. 7 is a diagram of the construction of plasmid BP892.

Acetoacetyl CoA reductase gene from pBP841 was then ligated into pEFBL21.3/SAR at the Cla/Xba site to generate pBP892. The construction is shown in FIG. 7.

Similarly a PHB synthase gene was added as a Xba/Cla fragment to generate pBP893.

e. Plant Transformation

We established a successful protocol for cultivar independent cotton transformation. Table 1 below shows typical transformation efficiencies obtained in three independent experiments.

TABLE 1

| Experiment | Explants Bombarded | Survived (%) | Total Transgenic (%) | Epidermal | Vascular |
|---|---|---|---|---|---|
| #1 | 13,292 | 6,475 (49%) | 33 (0.25%) | 24 (0.18%) | 9 (0.07%) |
| #2 | 10,913 | 6,057 (56%) | 45 (0.41%) | 36 (0.33%) | 9 (0.08%) |
| #3 | 12,278 | 5,368 (44%) | 17 (0.14%) | 10 (0.08%) | 7 (0.06%) |

The efficiencies range from a low of 0.14% to a high of 0.41%. Furthermore, we have shown that genes can be introduced into different cotton cultivars. Thus Delta & Pine 50, Delta & Pine 90, Sea Island, Pima S6, and Acala varieties have been transformed with particle bombardment protocol. The transgenes introduced are expressed in a predictable manner, depending on the promoter element. Examples are shown in Table 2 below.

TABLE 2

| | | Gene Expression | |
|---|---|---|---|
| Plasmid | Promoter & Gene | Tissue Specific | Constitutive |
| pEX101 pEX102 | E6 cotton promoter; Carrot extensin gene | Fiber | — |
| p4006 p4032 | E6 cotton promoter; Parathione hydrolase gene | Fiber | — |
| pBP877 | FbLate2-82A cotton promoter; Acetoacetyl Co A reductase | Fiber | — |
| p2117CAB$_{321}$ | Arabidopsis Cab promoter; β-glucuronidase | — | All tissues |
| p2119 | Cauliflower mosaic 35s promoter; β-glucuronidase | — | All tissues |
| G9-2117 | Cotton G9 promoter; β-glucuronidase | Pollen | — |
| p2114 | Cauliflower mosaic 35s promoter; Bialaphos resistance gene | — | All tissues |

Thus the transformation experiments validate that 1) particle bombardment protocol is cultivar independent 2) the genes linked to various promoters function in an appropriate manner (fiber specific or constitutive) and therefore genetic constructs and elements are correct and 3) multiple genes can be introduced into a plant to obtain coordinated expression.

Referring to Table 3, below, we generated a total of 19 transgenic cotton containing FbLate2-82A promoter and bioplastic synthesis enzymes, acetoacetyl-CoA reductase or PHB synthase. Sixteen of these were epidermal transformants and remaining three germlines.

TABLE 3

| | Seed Axes | Transgenic Plants Identified* | |
|---|---|---|---|
| Plasmid | Bombarded | Epidermals | Germline |
| BP 891 (FBLate2-82A (Red + 35s Pol) | DP50 10,862 | 5 | 2 |
| BP 893 (FbLate2-82A (Red$^1$ + Pol) | DP50 5,127 | 5 | 1 |
| BP 894 FbLate2-82A (Red$^2$ 35s Pol) | DP50 5,273 | 2 | — |
| BP 896 FbLate2-82A (Red$^2$ 35 Pol) | DP50 7,186 | 4 | — |

$^1$= Construct contains FbLate2-82A promoter (2.3 kb)
$^2$= Construct contains FbLate2-82A promoter (1.3 kb) an enhancer element and SAR.
*This is a partial list of transgenic plants identified and purified so far. Additional plants from these groups will be available in the future.

f. Analysis of Transgenic Plants containing FbLate2-82A promoter.

Acetoacetyl CoA reductase was assayed as described by Saito, et al., Arch. Microbiol. 114:211–217, 1977. The reaction mixture contained 100 mM Tris-HCl, pH 8.0; 0.12 mM NADPH, and bacterial lysate. The mixture was preincubated at room temperature for 3 minutes and monitored at 340 nm. Acetoacetyl CoA was added (0.02 mM) and the decrease in NADPH was measured at 340 nm for 5 minutes. The millimolar extinction coefficient for NADPH is 6.22. One unit of acetoacetyl CoA reductase catalyses the oxidation of 1.0 micromole of NADPH in 1 minute.

Protein concentrations were determined by the method of Bradford (Anal. *Biochem.* 72:248–254, 1976) using the BioRad micro-assay method and bovine serum albumin as the protein standard.

The transgenic plants containing bioplastic enzymes can be assayed in a similar fashion as described for the bacterial source. The extraction buffer was modified to contain 0.01% soluble polyvinylpyrrolidone.

We analyzed several epidermal transformants containing the 2.3 kb FbLate2-82A promoter and identified two plants that expressed acetoacetyl CoA reductase in fiber. Leaf, stem and flower tissues were negative for reductase activity. In fiber very low levels of reductase activity is observed in 10-day through 20-day fibers. Enzyme activity increased significantly in 20-day and older fibers (Table 4 and FIG. 8). Thus, the tissue and development specificities of acetoacetyl CoA reductase gene in transgenic cotton linked to FbLate2-82A promoter follow the pattern seen for FbLate-2 gene. These results suggest that FbLate2-82A promoter (2.3 kb) is fiber-specific and can be utilized in directing heterologous gene expression in transgenic cotton.

Several plants containing the shorter version of FbLate2-82A promoter, the 1.3 kb fragment, were also analyzed. In this case, the promoter also contained an enhancer and a scaffold attachment region (SAR) to reduce "position" effect. Five of the epidermal transformants were positive for reductase activity in fiber. The enzymatic activity was low in 10-day fibers but increased with fiber development. When we tested other tissues for reductase activity, we found that leaf and stem were positive for enzyme activity. Thus, it appears that the 1.3 kb version may have lost its tissue specificity. It is possible that a tissue-specific element is located upstream of 1.3 kb fragment. These results suggest that the shorter version of FbLate2-82A promoter (1.3 kb) may be used to direct heterologous gene expression in transgenic cotton, but may not show tissue-specific expression.

TABLE 4

Expression Characteristics of FbLate2-82A Promoter Fragments: Aetoacetyl CoA Reductase Activity in Transgenic Cotton

| Promoter | Plant # | Tissues Reductase Activity ($\mu$mol/min/mg) | | | Fiber Reductase Activity ($\mu$mol/min/mg) | | | | | | |
|---|---|---|---|---|---|---|---|---|---|---|---|
| | | Leaf | Stem | Flower | 10 day | 15 day | 20 day | 25 day | 30 day | 35 day | 40 day |
| FbLate2-82A 2.3 Kb | #8801 | — | — | — | 0.01 | 0.02 | 0.6 | 1.61 | 1.04 | 1.00 | 0.97 |
| | #10413 | — | — | — | 0.007 | 0.05 | 0.300 | 0.65 | 1.13 | | |
| FbLate2-82A 1.3 Kb | #10472 | 0.03 | 0.02 | — | 0.12 | 0.4 | 0.26 | 0.86 | 0.80 | 0.59 | 0.82 |
| | #16512 | — | 0.01 | — | 0.04 | 0.03 | 0.08 | 0.09 | 0.05 | 0.01 | |
| | #10481 | 0.02 | 0.01 | — | 0.04 | 0.06 | 0.18 | 0.21 | 0.19 | 0.17 | |
| | #10529 | — | 0.03 | — | 0.004 | 0.013 | 0.14 | 0.17 | 0.06 | | |

Note: Five more plants (10788, 10786, 10801, 10794, and 10804) containing FbLate2-82A, 1.3 Kb were tested for acetoacetyl CoA reductase and were found to be positive in leaves.

TABLE 5

Transgenic Cotton Expressing PHB in Fibers

| | Reductase | | PHB Synthase | | |
|---|---|---|---|---|---|
| Plant # | Promoter | Activity in Fiber $\mu$mol/min/mg | Promoter | Activity in Fiber dpm | PHB $\mu$g/gm Fiber |
| #8801 | FbLate 2-82A (2.3 Kb) | 0.61 | 35s | ND | 154 |
| #10596 | FbLate 2-82A (2.3 Kb) | 0.04 | 35S | ND | 166 |
| #10481 | FbLate 2-82A (1.3 Kb) | 0.18 | FbLate 2-82A (1.3 Kb) | 630,551 | 12 |
| #10472 | FbLate 2-82A (1.3 Kb) | 0.26 | FbLate 2-82A (1.3 Kb) | 453,733 | 46 |
| #10438 | FbLate 2-82A (1.3 Kb) | ND | FbLate 2-82A (1.3 Kb) | 275,232 | ND |
| DP50 control | — | — | — | 300,081 | — |

ND = Not done.

Moreover, as seen from the Table 5, both plants are expressing two enzymes necessary for bioplastic synthesis in fiber. HPLC analysis of the fibers prove that they contain bioplastic. Thus, FbLate2-82A promoters can be used for expressing heterologous protein to modify the fibers.

Figure 8A:
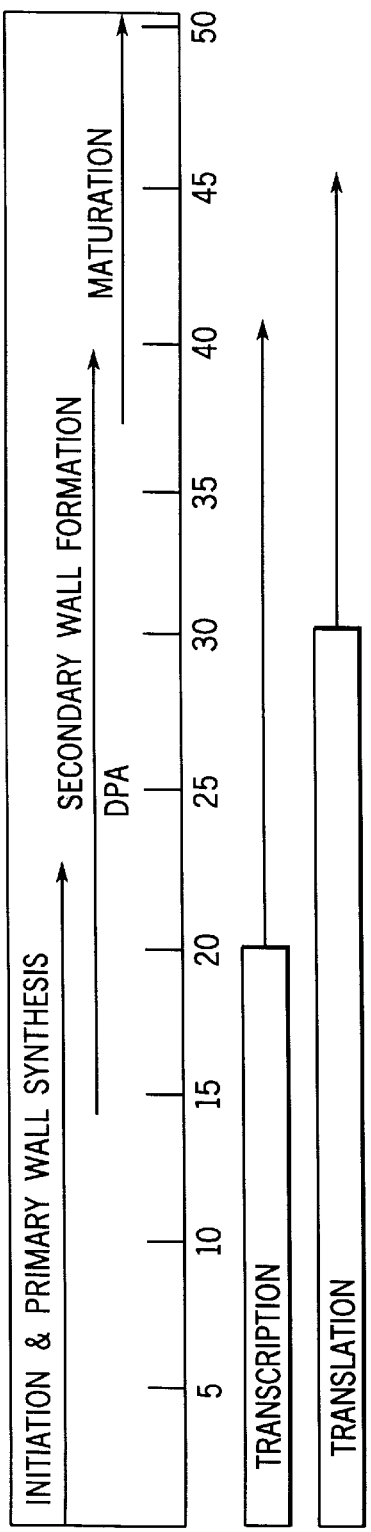
FIG. 8 is a chart of the measurements of acetoacetyl CoA reductase activity in developing fiber.
Figure 8C:
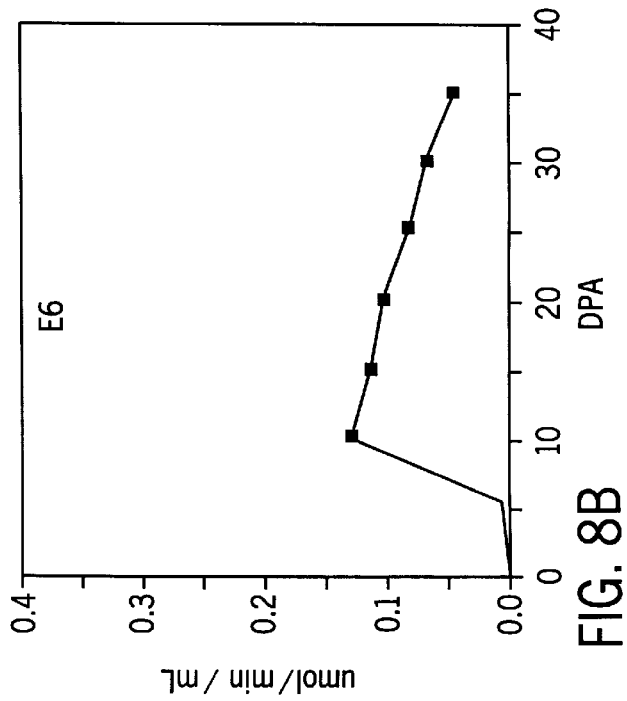
Figure 8B:
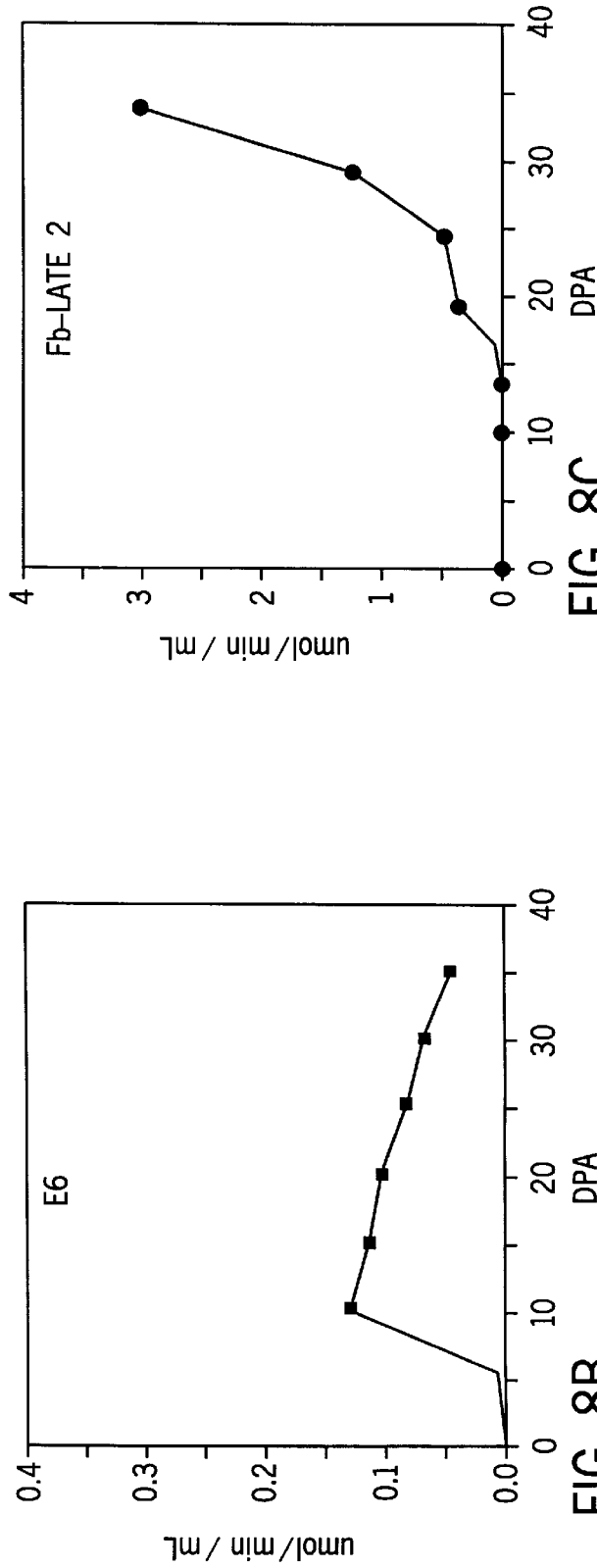

Various plant genes are known to be developmentally regulated. In case of the FbLate2-82A gene, we observed that the transcripts were not detected in the 10, 15-day fibers. In 23-day fibers the transcripts were present. This result suggested that the gene is activated late in fiber development. By linking a heterologous gene to FbLate2-82A promoter and examining its expression as a function of fiber development, we can assess the regulation of FbLate2-82A promoter during development. This result is shown in FIG. 8. Here we measured the acetoacetyl CoA reductase activity in developing fibers from two transgenic plants. Plant C8801 contains the reductase gene linked to FbLate2-82A promoter, whereas plant 5702 contains the reductase gene linked to a fiber specific promoter E6.

The FbLate2-82A promoter-linked gene shows very low activity during the early fiber development. The activity increases significantly at about 20-day. This result is in agreement with our earlier observation that FbLate-2 RNA was not detected in 10-day and 15-day fibers. The enzyme level decreases after 35 days. However there is still very high levels in 40- and 45-day fibers. In contrast, plant containing E6 promoter shows activity in early fiber development that decreases as development proceeds. Note that the C8801 achieves a 20-fold higher level enzymatic activity compared to C5702.

I claim:

1. A gene construct comprising an FbLate promoter, wherein the FbLate promoter comprises nucleotides 1 to 2315 of SEQ ID NO:3.

2. A transgenic plant comprising the construct of claim 1.

3. The plant of claim 2, wherein the plant is a cotton plant.

4. A plant seed comprising the construct of claim 1.

5. A plant cell comprising the construct of claim 1.

* * * * *